(12) United States Patent
Goradia

(10) Patent No.: US 6,179,850 B1
(45) Date of Patent: Jan. 30, 2001

(54) METHOD AND APPARATUS FOR MODULATING FLOW IN BIOLOGICAL CONDUITS

(76) Inventor: Tushar Madhu Goradia, 7-28 Point Crescent, Malba, NY (US) 11357

(*) Notice: Under 35 U.S.C. 154(b), the term of this patent shall be extended for 0 days.

(21) Appl. No.: 09/226,871

(22) Filed: Jan. 7, 1999

(51) Int. Cl.$^7$ ................................................ A61B 17/08
(52) U.S. Cl. ......................................................... 606/158
(58) Field of Search ................................. 606/158, 157, 606/151, 144, 213, 191; 128/898, 899

(56) References Cited

U.S. PATENT DOCUMENTS

| | | |
|---|---|---|
| 2,921,584 | 1/1960 | Di Vette . |
| 3,302,648 * | 2/1967 | Nelson ................................. 606/158 |
| 3,320,958 * | 5/1967 | Nolan ................................... 606/158 |
| 3,538,917 | 11/1970 | Selker . |
| 3,598,125 | 8/1971 | Cogley . |
| 3,786,816 | 1/1974 | Wolvek . |
| 3,972,333 * | 8/1976 | Leveen ................................. 606/158 |
| 4,016,883 | 4/1977 | Wright, Jr. . |
| 4,024,855 * | 5/1977 | Bucalo ................................. 128/899 |
| 4,337,774 | 7/1982 | Perlin . |
| 4,360,023 | 11/1982 | Sugita et al. . |
| 4,478,219 | 10/1984 | Rozario et al. . |
| 4,484,581 * | 11/1984 | Martin et al. ........................ 606/158 |

(List continued on next page.)

OTHER PUBLICATIONS

Commander L.H. Fink, MC, USN et al., A Comparative Study of Performance Characteristics of Cerebral Aneurysm Clips, 11 Surgical Neurology 179–186 (1979), Bethesda, Maryland.

Dujovny, Manuel M.D. et al. Temporary Microvascular Clips, vol. 5, No. 4, Neurosurgery 456–463 (1979), Pittsburgh, Pennsylvania.

Kossovsky, R. et al., Metallurgical Evaluation of the Compatibility of Surgical Clips with Their Appliers, 59 Acta Neurochirurugica 95–109 (1981), Pittsburgh, Pennsylvania.

Dujovny, Manuel M.D. et al. Intracranial Clips: An Examination of the Devices Used for Aneurysm Surgery, vol. 14, No. 3, Neurosurgery 257–267 (1984), Pittsburgh, Pennsylvania.

Atkinson, John L.D., M.D. et al., A Comparative Study in Opening and Closing Pressures of Cerbral Aneurysm Clips, vol. 26, No. 1 Neurosurgery 80–85 (1990), Rochester, Minnesota.

Primary Examiner—Michael H. Thaler
Assistant Examiner—(Vikki) Hoa B. Trinh
(74) Attorney, Agent, or Firm—Law Offices of Royal W. Craig

(57) ABSTRACT

An apparatus for modulating flow in biological conduits has a valve mechanism which has an open state and a closed state. The valve is applied and secured to a particular biological conduit while being maintained in an open state. An actuating mechanism is provided which actuates a change of state of the valve from an open state to a closed state in response to leakage from the biological conduit. In one embodiment, actuation is automatic and in another it is manual but remote. A preferred embodiment is a pinch valve such as that used in temporary micro vascular surgery to which is added an effectively resilient element interposed between opposing members of said clip. The interposed element is configured such that it is unable to maintain the clip in an open position unless the clip opening is augmented by manual or other means, and it is able to maintain the clip in an open position if a blood vessel is placed within the clip and has an adequate flow. Also in a preferred embodiment, the interposed element is ratcheted such that the clip is more readily changed from an open state to a closed state than it is from a closed state to an open state. A preferred embodiment for remote manual activation requires the resilient element to be partially ferromagnetic such that a manually activated magnetic field is sufficient to cause the leaf spring to trigger transition of the clip to a closed state.

38 Claims, 37 Drawing Sheets

U.S. PATENT DOCUMENTS

| | | |
|---|---|---|
| 4,531,519 | 7/1985 | Dunn et al. . |
| 4,708,140 | 11/1987 | Baron . |
| 4,765,335 | 8/1988 | Schmidt et al. . |
| 4,800,879 * | 1/1989 | Golyakhovsky et al. ............ 606/158 |
| 4,815,466 | 3/1989 | Perlin . |
| 5,454,826 | 10/1995 | Ueda . |

* cited by examiner

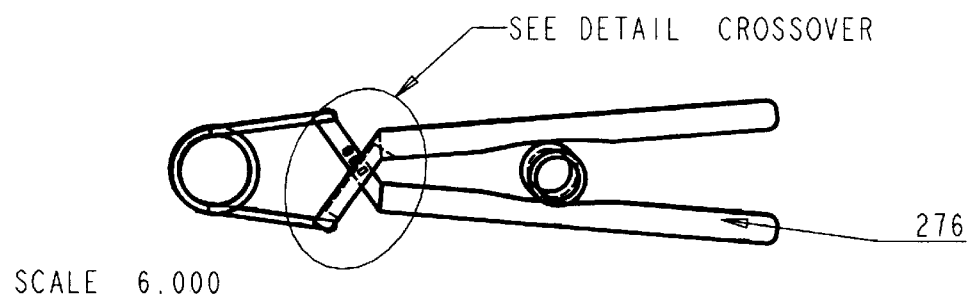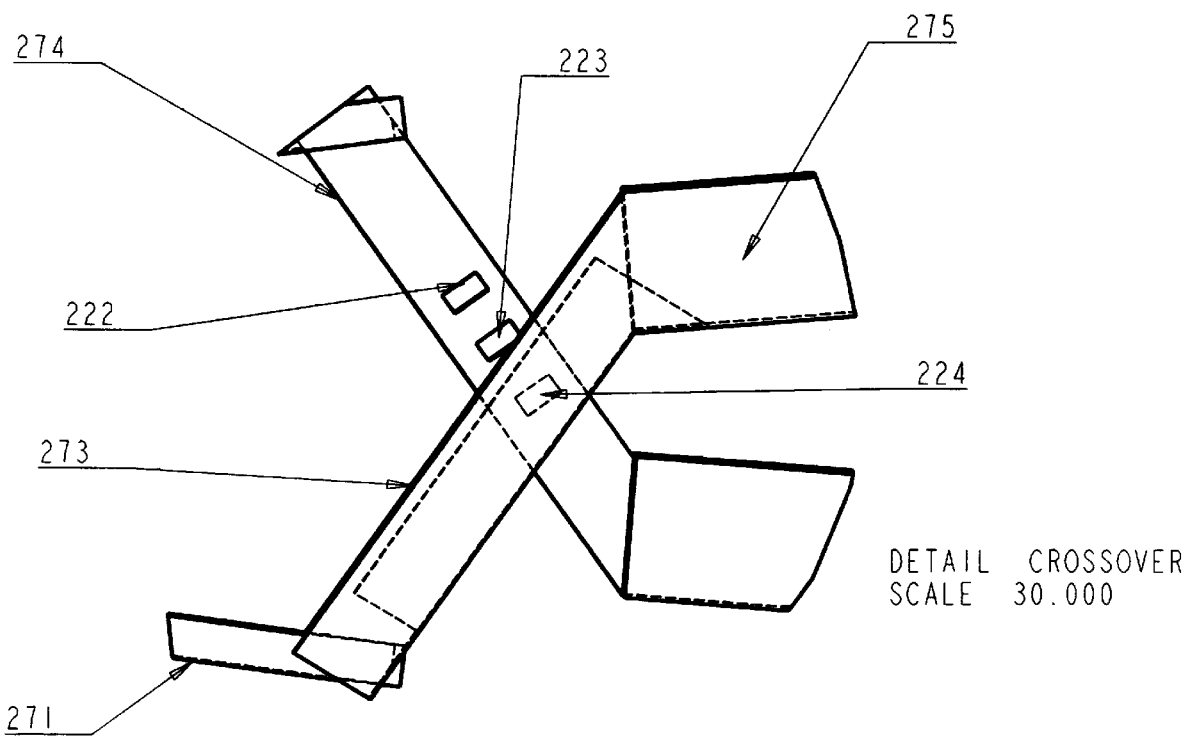
Figure 2 B

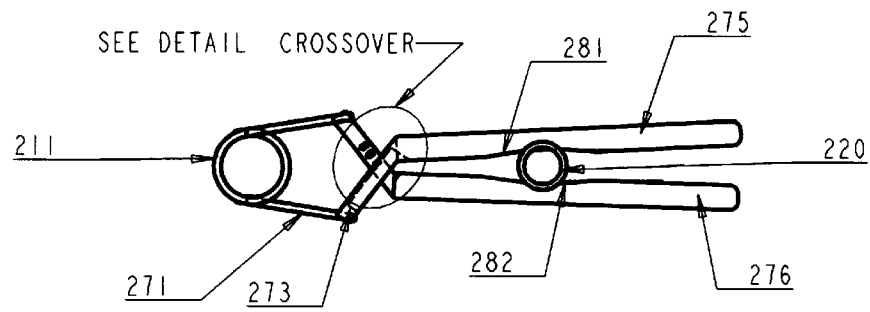
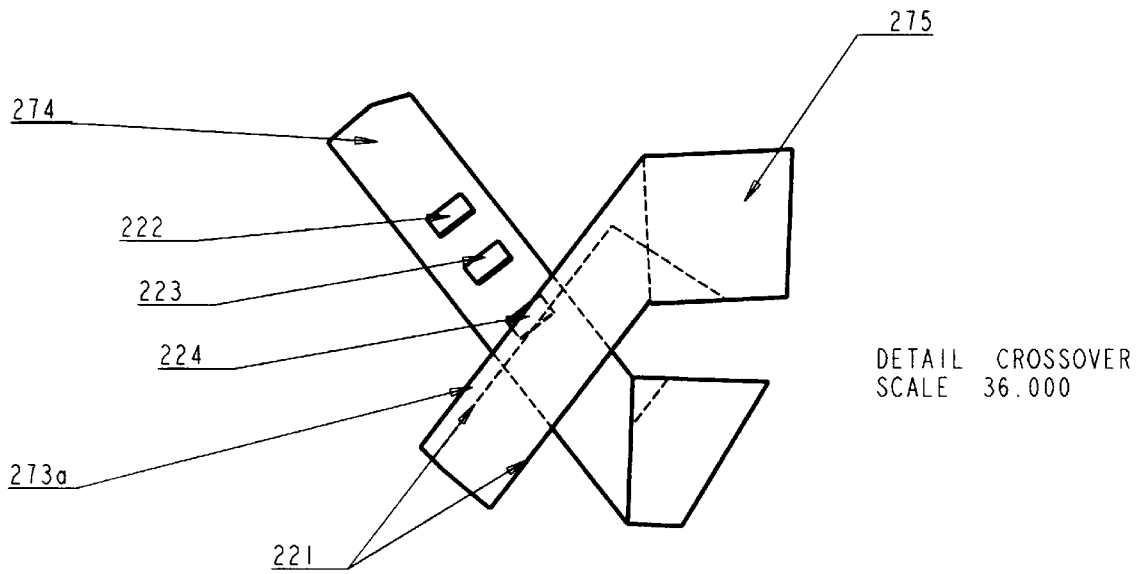
Figure 2 C

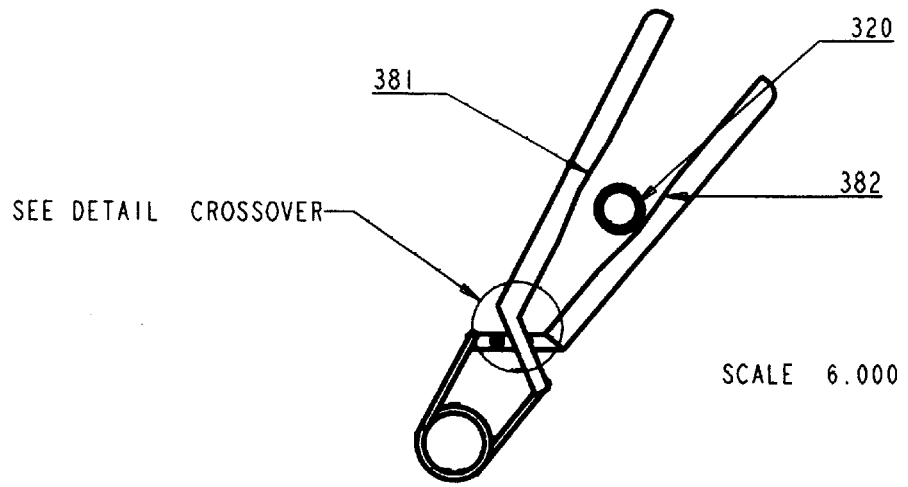
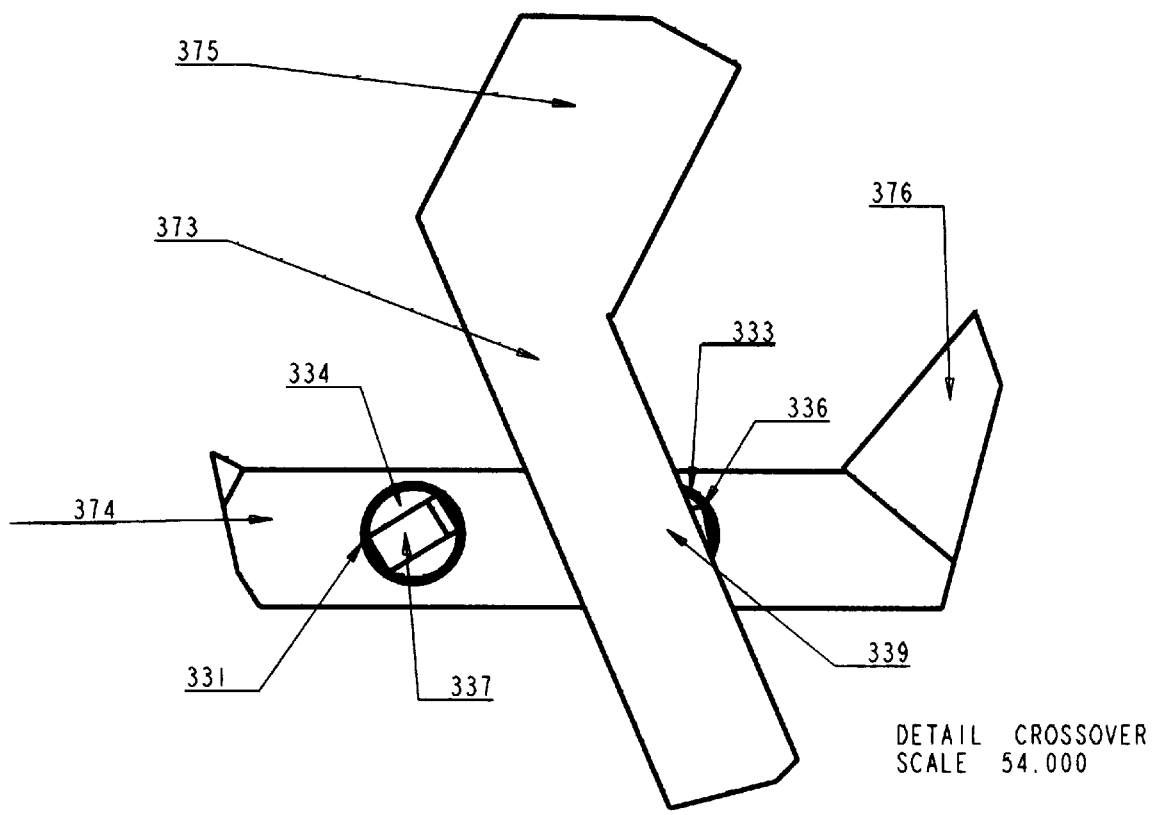
Figure 3C

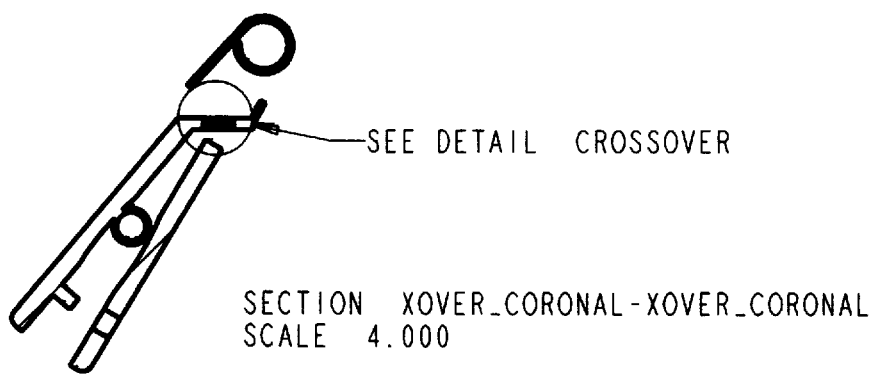
SECTION XOVER_CORONAL-XOVER_CORONAL
SCALE 4.000
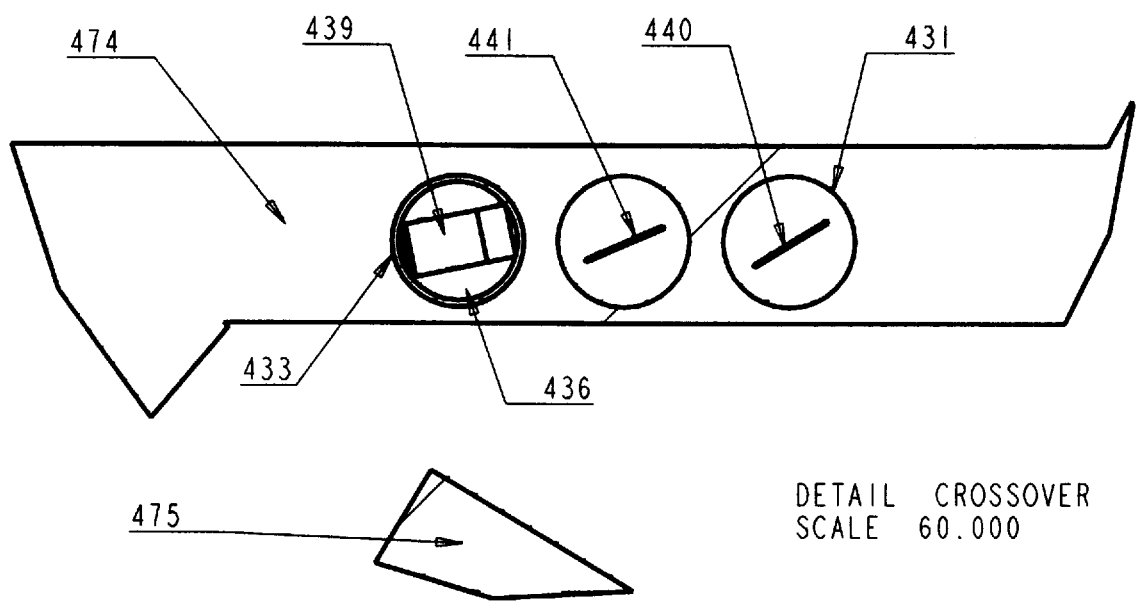
DETAIL CROSSOVER
SCALE 60.000
Figure 4D

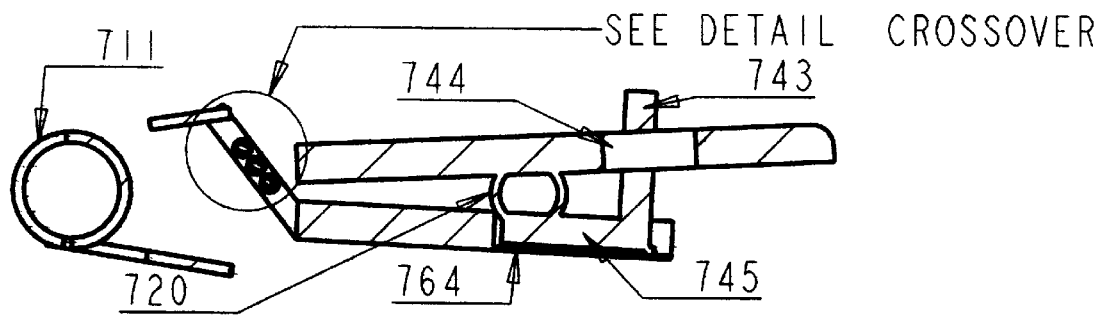
SECTION MIDSAGITTAL-MIDSAGITTAL
SCALE 6.000
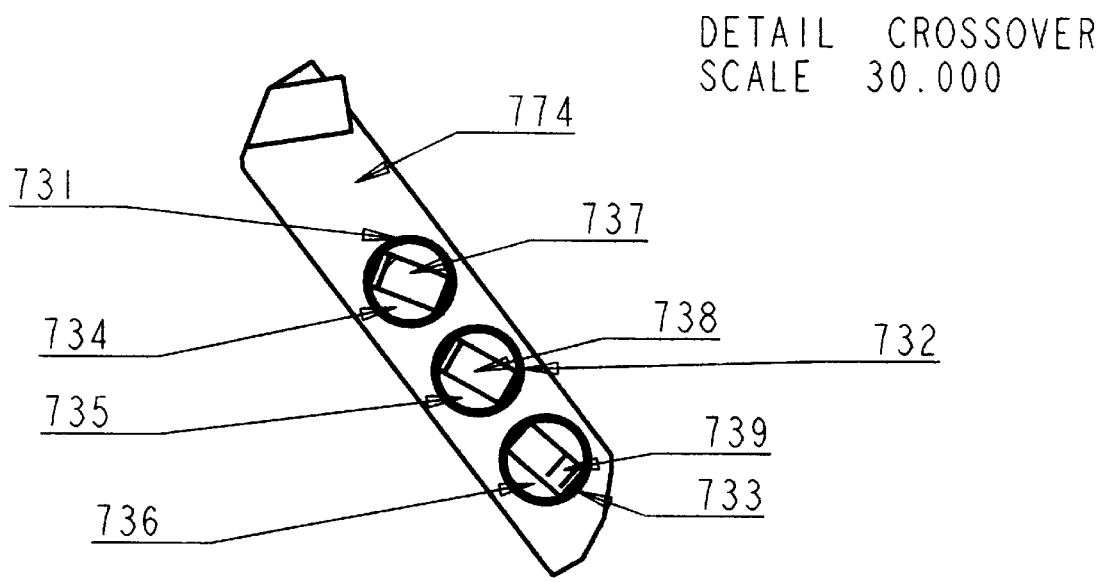
DETAIL CROSSOVER
SCALE 30.000
Figure 7D

METHOD AND APPARATUS FOR MODULATING FLOW IN BIOLOGICAL CONDUITS

BACKGROUND OF THE INVENTION

1. Field of the invention

This invention relates generally to the field of medical devices, and more particularly to an apparatus and method for modulating flow in biological conduits automatically and remotely.

2. Description of the Background

Invasive medical procedures subject blood vessels to the risk of perforation leading to hemorrhage. Such hemorrhage often obscures the actual site of vessel damage and thereby impedes expeditious repair of the damage. In surgery, when a blood vessel bleeds profusely, the usual method of controlling the bleeding is to evacuate blood from the surgical field so that the operator may visualize the site of hemorrhage and directly repair the damage. Methods of repair range from sacrifice of the blood vessel using ligatures or cautery to repair of the vessel wall using microsurgical techniques.

If bleeding is profuse, the process of hemorrhage leads to a vicious cycle in which as hemorrhage continues, the actual site of blood extravassation is more difficult to visualize due to blood obscuring the field. Fortunately, in many open surgical procedures, suction and irrigation devices are sufficient to help the surgeon stop the bleeding.

However, in certain procedures, such as repair of intracranial aneurysms and endoscopic surgery, suction and irrigation may not be adequate to prevent hemorrhage from causing irreversible harm. Such harm may be avoided if more expeditious hemostasis is achieved.

In aneurysm surgery, preventive measures may be taken to reduce the risk of serious hemorrhage. For example, a surgeon may employ temporary surgical clips which are applied to vessels which feed the aneurysm. The clips occlude blood flow to the aneurysm while the aneurysm repair is being performed and thereby reduce the risk of severe hemorrhage during the high-risk repair procedure. The clips are removed when the repair is completed.

Endoscopic procedures rely on a transparent view of the surgical field. When bleeding occurs, it obscures the surgeon's view and may make it impossible to continue the procedure, especially if the previously transparent fluid environment within which the tip of the endoscope is navigated is clouded by blood products.

The present invention is an improved method and device for modulating flow in biological conduits. The specific application which will be described is vascular occlusion for intracranial aneurysm surgery. Briefly, the prior art entails placing a pinch-valve-type clip around a vessel to reversibly occlude flow within it. The clip is often applied using a separate instrument, called a clip applier, which reversibly and controllably grasps the clip so that the surgeon may place the clip on a vessel, actuate (i.e., "close") the clip, and then release the clip from the applier. The surgeon may use the same clip applier to engage an already-applied clip, de-actuate (i.e., "open") the clip, and then remove it from the surgical field.

Existing vascular clips are designed to be safe, effective, and to provide a relatively unobstructed view of the operative field. They are usually made of a biocompatible, non-ferromagnetic material, such as one of the stainless steels (i.e., a chromium-containing alloy), titanium, or plastic. This disclosure pertains to any clip which has the following elements:

(1) a resilient element responsible for self-closing of the clip, such as a coil spring or a leaf spring; and (2) two opposing jaw members (also known as "blades") which provide the active surfaces between which a vessel may be pinched to limit or occlude flow.

Some additional embodiments also rely on the presence of two opposing arm elements located proximally on the clip which permit one to open the clip by approximating these elements using, for example, a clip applier.

Further embodiments of the invention are possible by modifying a certain category of clips, known as alpha clips, which, in addition to the aforementioned elements also contain a "crossover region" where crossing elements, referred to as the "crossovers," change their relative positions depending on the degree to which the clip is open.

Besides alpha clips, the most commonly-used clips are pivot clips and mobile-fulcrum clips [illustrated on page 460 of the article by Dujovny et al., entitled *"Temporary microvascular clips,"* and found in the journal Neurosurgery, Volume 5 (1979)]. Briefly, these three categories of clips are distinguished as follows:

(1) alpha clips resemble the Greek letter "alpha" and contain a proximal helical spiral or leaf spring on each end of which emerges an arm; the arms have extensions, known as "crossovers", which cross over one another en route to their corresponding jaws; the fulcrum of this clip lies proximally and is fixed in location; such a clip is shown in FIGS. 0A, 0B, and 0C;

(2) pivot clips, in contrast to the alpha clips, have a fulcrum point in between the arms and the jaws; an example of such a configuration is seen in an ordinary clothespin;

(3) mobile-fulcrum clips have a moveable fulcrum point the position of which depends on the magnitude of the gap between the jaws.

While the present disclosure is described using alpha clips as an example, the first and sixth embodiments set forth below may be applied to pivot clips and mobile-fulcrum clips (the sixth embodiment requires the presence of "arms" as defined above).

The descriptions provided herein allow one reasonably skilled in the materials and mechanical arts to modify an existing vascular clip to create an embodiment of the invention. Of course, one may de novo construct a clip by combining the designs of a present clip with the modifications of the present invention specified herein. The generic elements, named "main spring," "arm," and "jaw" refer to the corresponding elements in any alpha clip, pivot clip, or mobile-fulcrum clip. In addition, the element "crossover" refers to the element between an arm and its corresponding jaw in any alpha clip.

Construction of the invention from an existing clip involves:

(1) removal of parts of existing components of the clip, e.g., by drilling or machining;

(2) creating new components of the clip which, unless otherwise specified, can be made of the same material used for the clip;

(3) attaching new components to the clip or its modification, such as simple insertion in the case of inserting a hinge into its sockets, or such as welding as in the case of affixing a leaf spring to an arm.

There is an abundance of types, sizes, and shapes of vascular clips, and it should be noted that the present invention may be applied to any of these. It should also be noted that for the present state of art, a surgeon may have a general idea of the clip to be used in a particular situation, but often will not know a priori which particular clip to use; the surgeon may rely to some degree on trial-and-error to find the perfect match for a particular patient's anatomy and physiology at a given point in time during the surgical procedure.

The following published articles are of value in understanding the present state of art:

(1) J L D Atkinson, R E Anderson, and D G Piepgras (1990). A comparative study in opening and closing pressures of cerebral aneurysm clips. Neurosurgery 26: 80–85.

(2) M Dujovny, N Kossovsky, R Kossowsky, A Perlin, R Segal, F G Diaz, and J I Ausman (1984). Intracranial clips: An examination of the devices used for aneurysm surgery. Neurosurgery 14: 257–267.

(3) R Kossowsky, M Dujovny, and N Kossovsky (1981). Mettalurgical evaluation of the compatibility of surgical clips with their appliers. Acta Neurochirurgica 59: 95–109.

(4) M Dujovny, N Kossovsky, R K Laha, L Leff, N Wackenhut, and A Perlin (1979). Temporary microvascular clips. Neurosurgery 5: 456–463.

(5) L H Fink, R E Flandry, R A Pratt, and C B Early (1979). A comparative study of performance characteristics of cerebral aneurysm clips. Surgical Neurology 11: 179–186.

Several earlier patents have addressed the need to controllably occlude blood vessels. For example, a device for remote occlusion of a blood vessel using a pinch valve mechanism is described in U.S. Pat. No. 2,921,584. However, the apparatus is not an automatic means for such occlusion, and the device requires a tubular connection from the occlusion valve to the actuator. The balloon-occlusion clip described in U.S. Pat. No. 3,538,917 uses balloon inflation but has similar shortcomings.

The vascular conduit tourniquet described in U.S. Pat. No. 3,786,816 is another means for temporary occlusion of blood vessels but once again does not provide for an automatic means of a non-contiguous actuator.

The micro surgical clip described in U.S. Pat. No. 4,337,774 uses a resilient rod/ratchet mechanism to control the closing force of the clip, and again fails to provide for automatic or wireless actuation of the clip.

The temporary microvascular occluder described in U.S. Pat. No. 4,478,219 discloses magnetically moving the occluding device into and out of a clamping position. However, the mechanism of actuation fails to provide automatic actuation of the device.

The inflatable vascular clamp described in U.S. Pat. No. 4,531,519 likewise lacks automatic or wireless actuation.

The atraumatic vascular balloon clamp described in U.S. Pat. No. 4,708,140 also lacks automatic or wireless actuation.

The temporary clip comprising an inflatable balloon for controlling blood flow described in U.S. Pat. No. 5,454,826 permits remote-controlled clip actuation, but once again the means of actuation is a physical link coupled to the clip mechanism which fails to automatically achieve a flow-stopping state. Also, actuation to an indefinite flow-stopping state is not automatic. What is described as automatic is the clipping pressure, but not clip activation.

Existing methods for hemostasis during aneurysm surgery are of two major types. The first is a preventive method. One example is the placement of temporary vascular clips on tributaries to potential sites of hemorrhage. With such clips in place, the chance of profuse bleeding is reduced, but the risk of stroke-like complications increases with the duration of temporary clipping. Another example of the preventive method involves having endovascular balloons in place prior to the procedure. The balloons, when activated, will occlude further blood flow to the site of hemorrhage. Once the hemorrhage is controlled, the balloons can be inactivated, thereby restoring blood flow to the brain.

Although temporary clips which can be remotely activated have been previously known, they are not commonplace in operating rooms. The main reason for this is that the means of activation is a direct physical link coupled to the clip. Such a link, such as flexible tubing, clutters the operative field and also may interfere with other operating instruments; for example, a sharp dissector may accidentally perforate the flexible tubing. Microsurgery demands maximal visualization with minimal clutter in the field; the earlier art falls short of these requirements.

The second method of hemostasis during aneurysm surgery is the direct method which involves suctioning away blood to clear the field and then identifying the source of bleeding which is then repaired by one of a number of means such as vessel sacrifice, electrocautery, vascular clipping, or vessel repair.

Existing methods for hemostasis during endoscopic surgery rely on quickly identifying the source of bleeding and using techniques such as electrocautery to repair the vessel. However, in the event of significant bleeding, the surgeon may not have the necessary time or visualization to achieve such hemostasis in which case the entire endoscopy procedure may have to be altogether aborted.

Existing methods for treating unclippable aneurysms include endovascular coiling and aneurysm wrapping. Despite these methods, aneurysm rupture can still occur. Morbidity and mortality from aneurysm rupture relate to the degree of intracranial hemorrhage. The presence of an automatic, rupture-activated clip can forestall significant bleeding and help reduce the complications of intracranial hypertension, vasospasm, and hydrocephalus from bleeding.

SUMMARY OF THE INVENTION

One primary object of the present invention is to provide an apparatus and method for modulating flow in biological conduits remotely and/or automatically.

A further object of the invention is to modify existing surgical clips so that they may modulate flow in biological conduits remotely and/or automatically.

Another object of the invention is to provide an apparatus to modulate flow in biological conduits which may be secured to a biological conduit while permitting ordinary flow prior to actuation.

Yet another object of the invention is to provide an apparatus to modulate flow in biological conduits with minimal cluttering of the space around the conduit.

Another object of the invention is to provide an actuating apparatus which automatically changes flow in a biological conduit in response to detecting leakage from it or a contiguous conduit.

A further object of the invention is to provide an actuating apparatus which changes flow in biological conduits in response to entirely remote actuation.

Another object of the invention is to provide an apparatus to modulate flow in biological conduits through selective use of either remote means or direct manual actuator means.

Yet another object of the invention is to provide an apparatus to modulate flow in biological conduits which may be remotely operated to permit a biological conduit to resume its ordinary flow after its flow has been modulated.

A further object of the invention is to provide an apparatus to modulate flow in biological conduits by exerting less pressure on the conduits to accomplish the same goal as the prior art.

In accordance with the above objects, an improved method and apparatus for modulating flow in biological conduits is disclosed. The apparatus of the present invention comprises a valve mechanism which has an open state and a closed state. The valve is provided with means for applying the valve to and removing the valve from a biological conduit and positioning the valve thereon while maintaining the valve in an open state. The valve also comprises an actuating mechanism which automatically actuates a change of state of the valve from an open state to a closed state in response to a leakage condition occurring within the biological conduit or one contiguous with it. The valve is also provided means for selectively remotely actuating the valve, instead of allowing the valve to automatically actuate, to allow the operator to change the state of the valve from an open state to a closed state whenever the operator desires to do so. Further, the valve is configured to remain in each particular state, whether open or closed, until it is manually or remotely reset to another state.

The preferred embodiment of the invention is a temporary vascular clip which functions as a self-closing spring-driven pinch valve to reversibly clamp a vessel shut, thereby stopping blood blow. The clip has its native jaw-closing mechanism, such as a helical tension spring, henceforth referred to as the "main spring," which provides the force necessary to pinch closed a blood vessel; it also has a jaw-opening mechanism which separates the jaws only if the pressure within the vessel is above a desired level; if the vessel suddenly bleeds, pressure within the vessel will drop, the force exerted by the vessel on the jaws will correspondingly drop, and the jaw-opening mechanism will give way to the tension exerted by the main spring, thereby closing the clip. The jaw-opening mechanism is actuated only after the clip is placed on a vessel; in addition, a vessel-guarding mechanism prevents the vessel from slipping out of the clip. A restraining mechanism prevents the clip from reopening on its own when intravascular pressure is restored.

In its general form, the invention can be applied to any biological conduit. Flow within the conduit can be modulated by automatic, remote, and manual means. The method and apparatus of the present invention may be applied not only in the treatment of aneurysms, but in any surgical procedure in which a risk of hemorrhage or viscus perforation is present, including but not limited to bowel surgery, endoscopic procedures, and endovascular procedures.

BRIEF DESCRIPTION OF THE DRAWINGS

Other objects and advantages of the present invention will become apparent from the following descriptions, taken in connection with the accompanying drawings, wherein, by way of illustration and example, an embodiment of the present invention is disclosed. The drawings constitute a part of this specification and include exemplary embodiments to the invention, which may be embodied in various forms. It is to be understood that in some instances various aspects of the invention may be shown exaggerated or enlarged to facilitate an understanding of the invention.

The function and advantage of this invention will become more apparent from the following description taken in connection with the accompanying drawings in which:

FIG. 3C illustrates the detail of the crossovers of the clip of FIG. 3A from the side.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 0A:
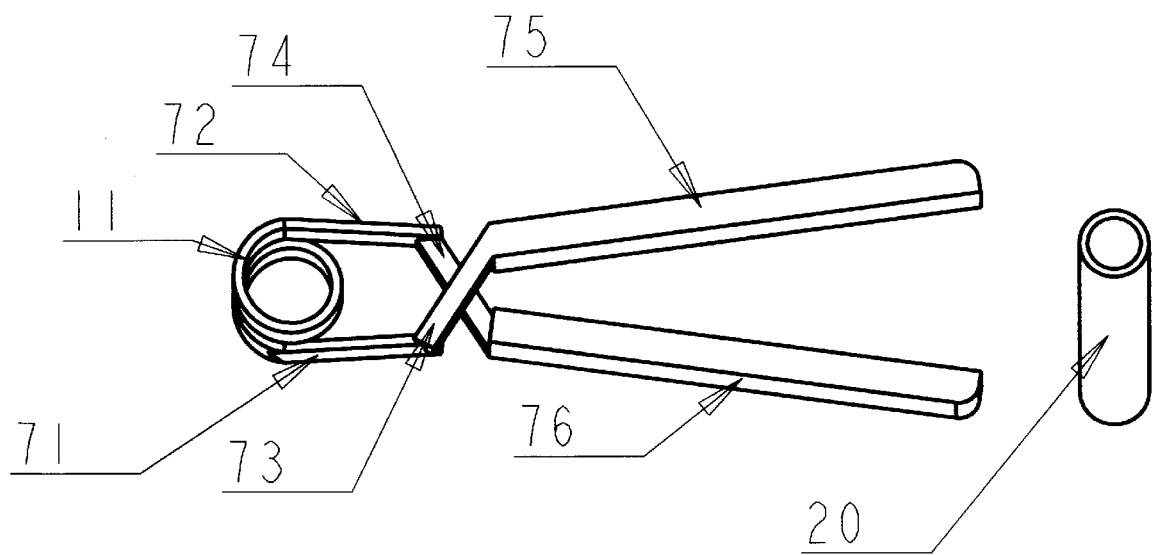
FIG. 0A is a perspective view of a temporary vascular clip (prior art).
Figure 0B:
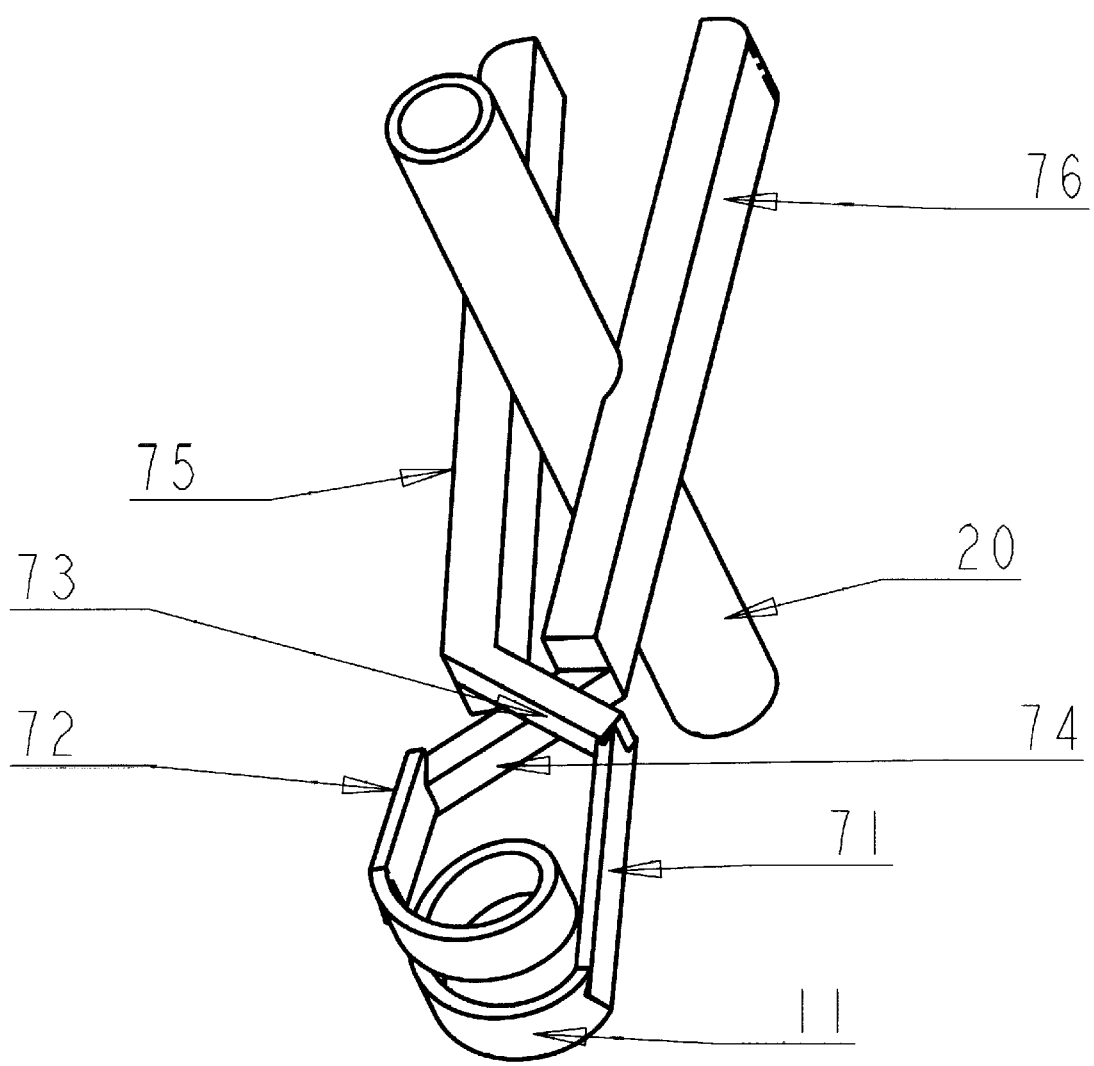
FIG. 0B is a perspective view of a temporary vascular clip (prior art) applied to a blood vessel.
Figure 0C:
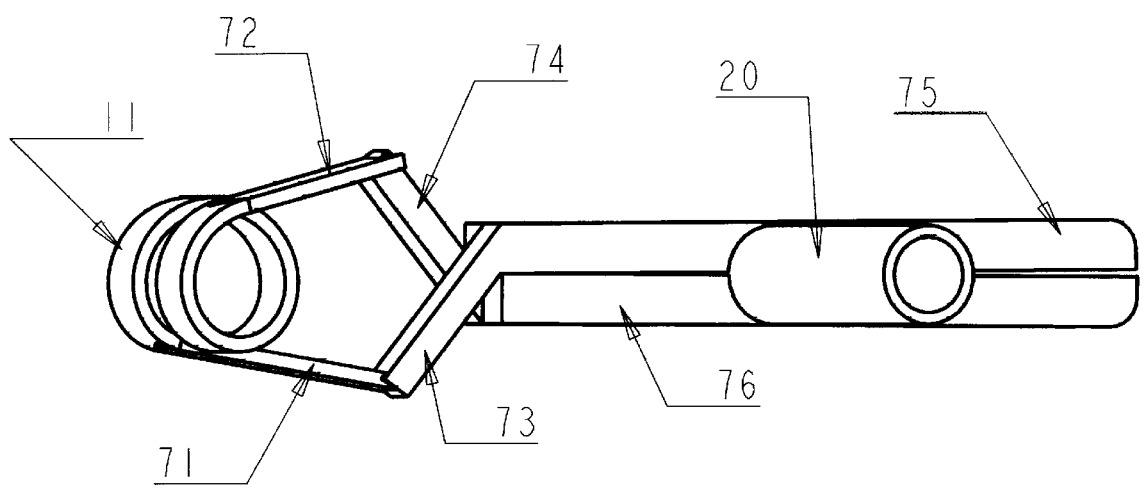
FIG. 0C is a perspective view of a temporary vascular clip (prior art) in the closed state, resulting in occlusion of the blood vessel.

While the invention modulates flow in any biological conduit, a preferred embodiment involves conduits which are blood vessels and pinch valves which are vascular clips, such as that illustrated in FIGS. 0A, 0B, and 0C. The clip in FIGS. 0A, 0B, and 0C is a typical alpha-type vascular clip used for intracranial aneurysm surgery. The clip can be applied to a blood vessel or to an aneurysm which arises from a blood vessel. The former application is a means for temporarily stopping blood flow to the region of the aneurysm, whereas the latter is a means to obliterate the aneurysm. In both cases the clip operates by pinching the vascular structure closed.

The clip as illustrated in FIGS. 0A, 0B, and 0C comprises a main spring 11 on each end of which extends an arm 71, 72. From each arm extends its corresponding crossover 73, 74, and from the crossover extends its corresponding jaw 75, 76. The internal surfaces of the jaws 75, 76 are the active pinching surfaces between which a blood vessel ultimately lies. Although not illustrated, the pinching surfaces of the jaws 75, 76 are usually grooved to facilitate gripping of a blood vessel.

An open state of the clip corresponds to the clip not occluding the blood vessel 20 to which it is secured, as seen in FIG. 0B. A closed state of the clip, as seen in FIG. 0C, corresponds to the clip pinching the blood vessel sufficiently to restrict flow and thereby effect hemostasis.

Each embodiment of the invention can be constructed by modifying prior surgical clips. The specifications provided herein will describe methods for constructing the invention from a prior clip, such as that shown in FIGS. 0A, 0B, and 0C. In each case, unless otherwise specified, the material added to a prior clip is to be the same as that used to make the original clip. Most clips used today are made of corrosion-resistant cobalt-and chromium-based alloys, such as cobalt-chrome alloy or cobalt-chromium-molybdenum alloy, which are biocompatible, durable, and nonferromagnetic; however, some of the newer clips are made of plastic or chemically pure titanium in an attempt to minimize artifact on magnetic resonance imaging studies.

It should be noted that during aneurysm surgery, the surgeon will often try out several types, shapes, and sizes of existing clips to see which best suits the patient's particular anatomy and physiology. Indeed, the surgeon is provided with an "aneurysm clip tray" which has an assortment of clips.

Each embodiment of the present invention can be applied to any prior alpha clip, but the descriptions below will refer to the particular alpha clip shown in FIGS. 0A, 0B, and 0C. In addition, each embodiment applies to pivot clips and mobile-fulcrum clips, unless otherwise noted.

The common elements among the clips to which the present invention applies are the jaws 75, 76 and the main spring 11. The sixth embodiment disclosed below (FIGS. 6A to 6D) relies on the presence of arms 71, 72 which the aneurysm-applying tool grasps to insert the clip onto a vessel. In addition, alpha clips have crossover limbs 73, 74 connecting the arms to the jaws, and these are utilized by the second, third, fourth, and fifth embodiments set forth below.

The invention, in its generality, employs the following elements:

(1) a mechanism to keep the jaws open when vascular pressure is normal;
(2) another mechanism to cause the jaw-opening mechanism to fail when pressure within the vessel drops below a threshold level; and
(3) a mechanism to help secure a blood vessel within the jaws.

In addition, an optional mechanism to help keep the jaws shut until opened by the operator is described.

With regard to dimensions and tolerances, as mentioned previously a surgeon will often try out a variety of clips to see which best suits the particular situation; this is referred to as the "art" of clip selection and often is not reproducible within a group of surgeons. However, what can be said about vascular clips for intracranial surgery is that they are characterized by the following parameters:

(1) jaw length (the most commonly used jaw lengths are between 6 and 14 mm.);

(2) gap distance between the tips of the jaws when the clip is open (the most common gap distance for a surgeon to use when applying a clip is from 0.5 to 3.0 mm.);

(3) position along the jaw where the vessel is to sit (most often between 15% and 50% of the jaw length, measured from the tip);

(4) closing force at the position where the vessel sits, defined as the amount of tension a clip exerts on a vessel, when closed (usually between 10 and 220 grams as measured by a clip tension meter); and (5) opening pressure at the position where the vessel sits, defined as the millimeters of Mercury arterial pressure required to open a clip which has already pinched close an artery (usually between 60 and 600 mm. Mercury).

While the present invention is suitable for aneurysm obliteration, its particular value is for the temporary clipping of blood vessels. Temporary vessel clipping differs from permanent clipping in that the vessel is intended to be preserved; hence, the clip should minimize damage to the vessel wall by utilizing as small an occlusion force as possible. Fortunately, the invention allows one to further reduce clip occlusion force since the force is only applied when an artery has bled and therefore when the artery has a lower-than-normal intravascular pressure which the clip must oppose.

FIGS. 1A, 1B, 1C, 1D, 1E, and 1F illustrate a first preferred embodiment of the invention as a modification of the alpha vascular clip illustrated in FIGS 0A, 0B, and 0C. The new clip comprises the elements of the clip illustrated in FIG. 0A and also has an L-shaped element 145, henceforth referred to as the "vessel guard," hinged to the foreshortened distal portion of the bottom jaw 176. A straight vertical protrusion 168, henceforth referred to as a "vessel stop," is preferably provided on the proximal portion of the bottom jaw 176 which is a fence to prevent backward slippage of the vessel.

Figure 1A:
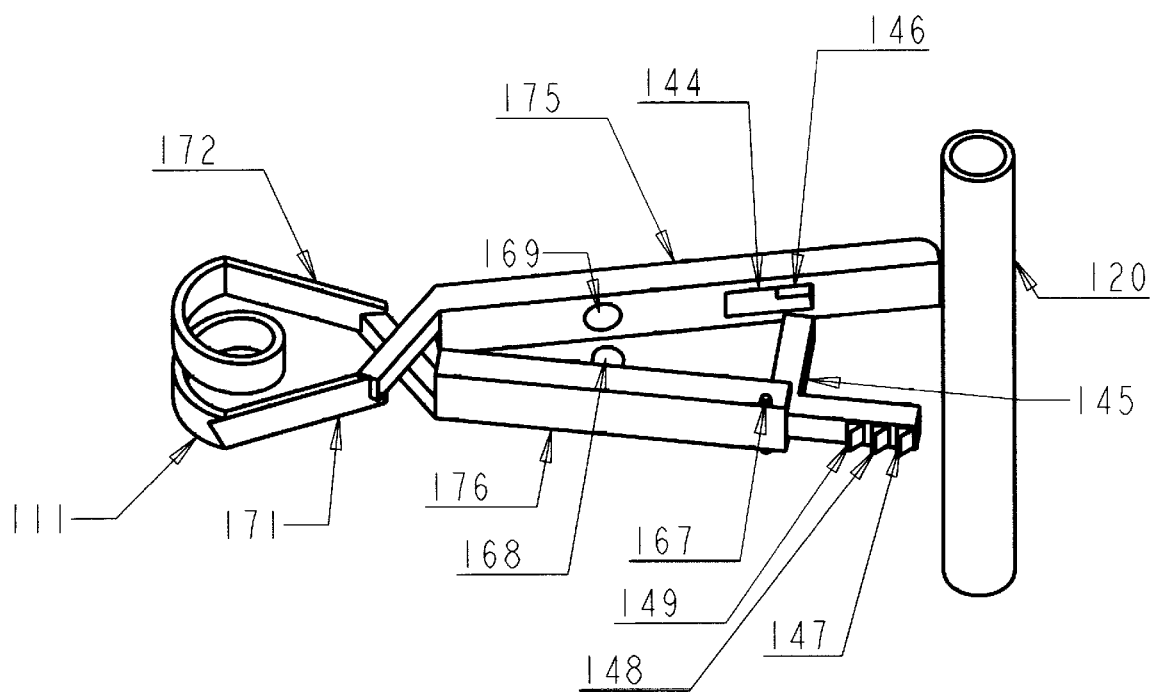
FIG. 1A is a perspective view of a preferred embodiment of the invention illustrating a L-shaped element hinged to the lower jaw.
Figure 1B:
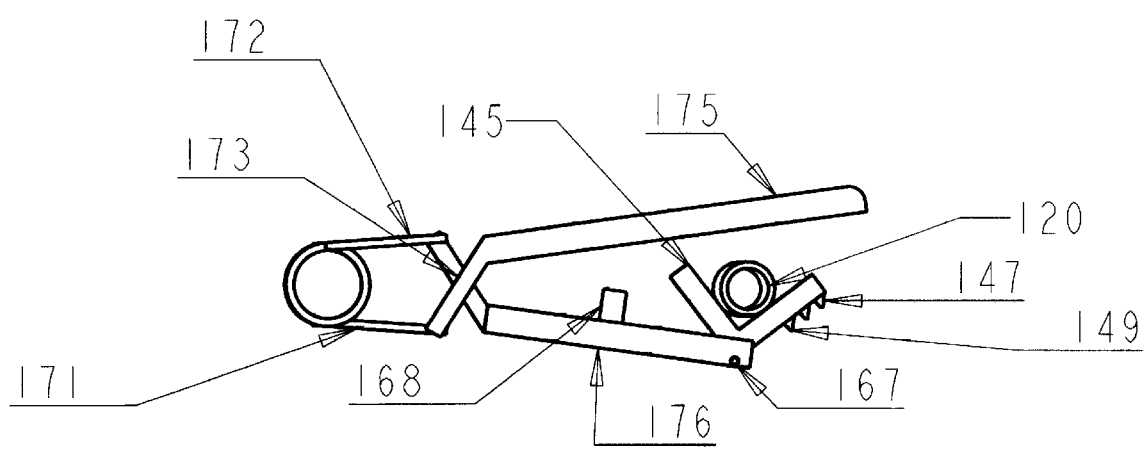
FIG. 1B is a side view of the clip of FIG. 1A being applied to a blood vessel.

The vessel guard 145 serves as a mechanical relay to actuate the hemorrhage-sensing component of the invention. When the clip is applied to a blood vessel, as seen in FIG. 1B, the vessel guard 145 is rotated about its hinge 167 such that the proximal element lies in a trough 164 (FIG. 1C) within the bottom jaw 176. As the clip is closing over the vessel, the distal portion of the vessel guard 145 is forced to lie in a vertical position and its tip enters a slot 144 in top jaw 175, henceforth referred to as the "vessel-guard slot." When the distal portion of the vessel guard 145 is horizontal, i.e., flush with the bottom jaw, we refer to it as "inactive"; when the distal portion of the vessel guard 145 is vertical, i.e., perpendicular to the bottom jaw 176 , we refer to it as "active"; in all other configurations it is "in transition."

Figure 1C:
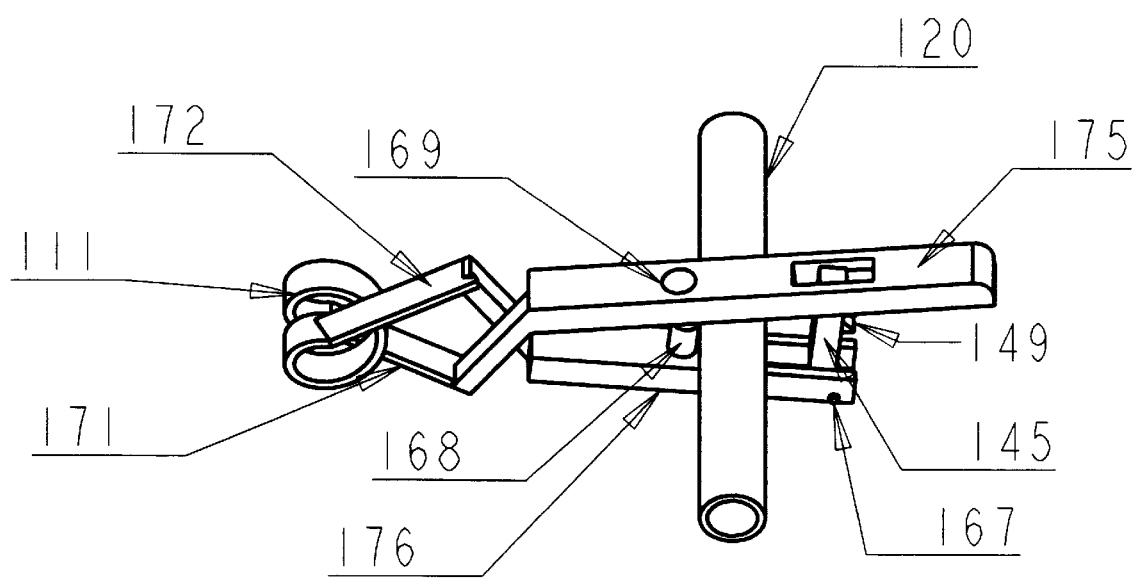
FIG. 1C is a perspective view of the clip of FIG. 1A applied to a blood vessel and with the vessel-guarding mechanism actuated.

As best seen in FIG. 1C, the vessel stop 168 helps keep the vessel guard 145 active by forcing the vessel to sit on the proximal portion of the vessel guard 145.

Figure 1D:
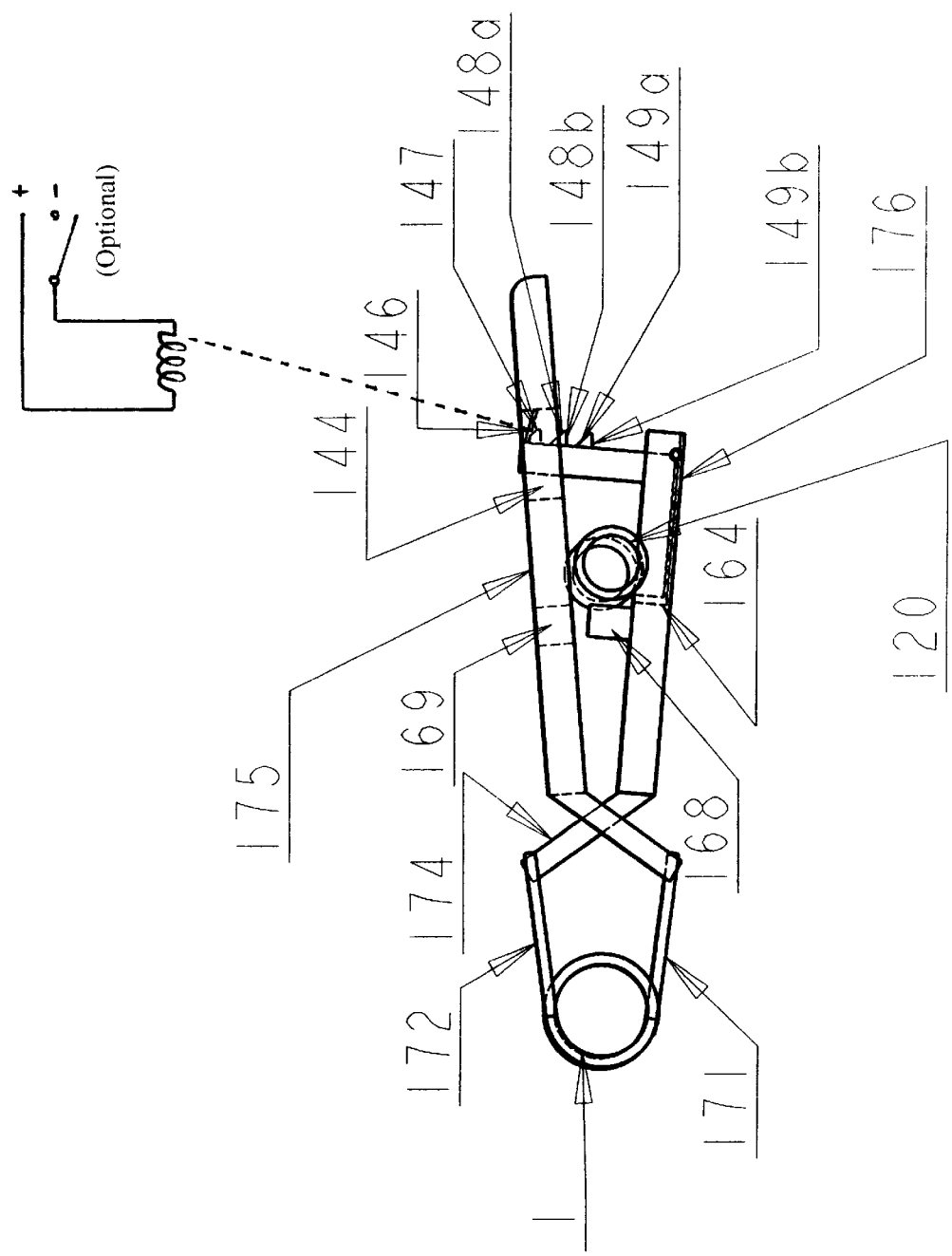
FIG. 1D is a side view of the clip of FIG. 1A secured to a blood vessel and triggered to close should the vessel hemorrhage.
Figure 1E:
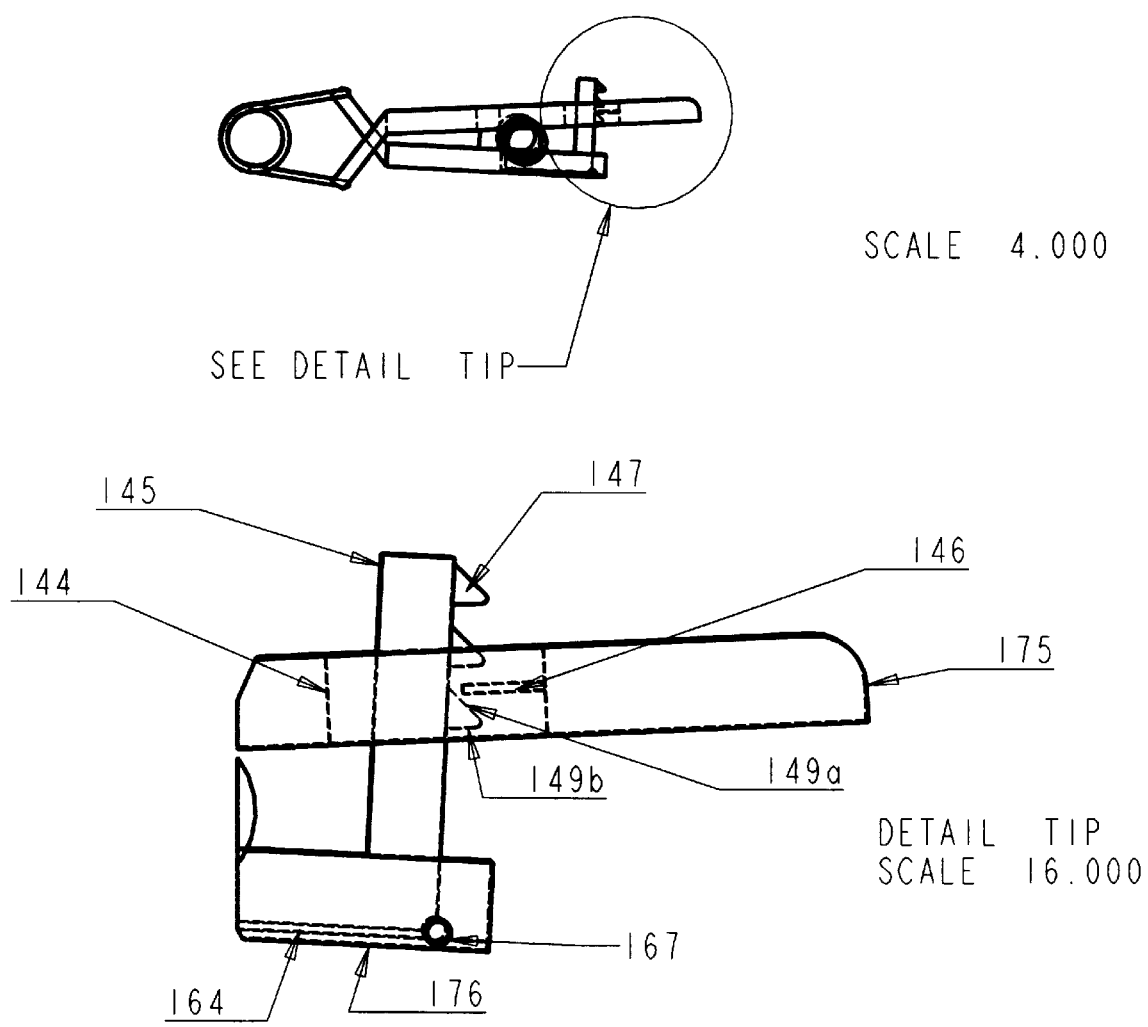
FIG. 1E is a detailed side view of the tip of the clip of FIG. 1A secured to a blood vessel and in transition from an open state to a closed state.

FIGS. 1D and 1E demonstrate the hemorrhage-sensing component. On the outer surface of the vessel guard 145 is an array of wedge-shaped protrusions 147, 148, 149, henceforth referred to as "teeth" (more than one tooth is present to allow for a wider range of vessel sizes for a particular embodiment of the invention to apply to). A leaf spring 146 acts upon the vessel guard 145 as a detent with limited holding strength. FIG. 1D demonstrates how the topmost tooth 147 engages the leaf spring 146 and transmits the tension of the main spring 111 to bend the leaf spring 146 upwards. However, the bias of the leaf spring 146 prevents it from being bent sufficiently for the tooth 147 to pass above it, so long as the vessel 120 has a normal blood pressure. If the vessel 120 bleeds and thereby loses its blood pressure, the vessel 120 will no longer be able to assist the leaf spring 146 in sustaining the force of the main spring 111 to keep the jaws 175, 176 open, and the clip will close. FIG. 1E demonstrates the clip in transition to a closed state, with the topmost tooth 147 having passed beyond the leaf spring 146. The nearly level bottom surface 149b of the teeth serves to make clip re-opening require a significant force of friction between the surface of the leaf spring 146 and the bottom surface of the tooth 149b; hence, the clip, once closed, will not reopen unless the surgeon intervenes; i.e., manual force by the surgeon is sufficient to re-open the clip to remove it or to reset it.

Figure 1F:
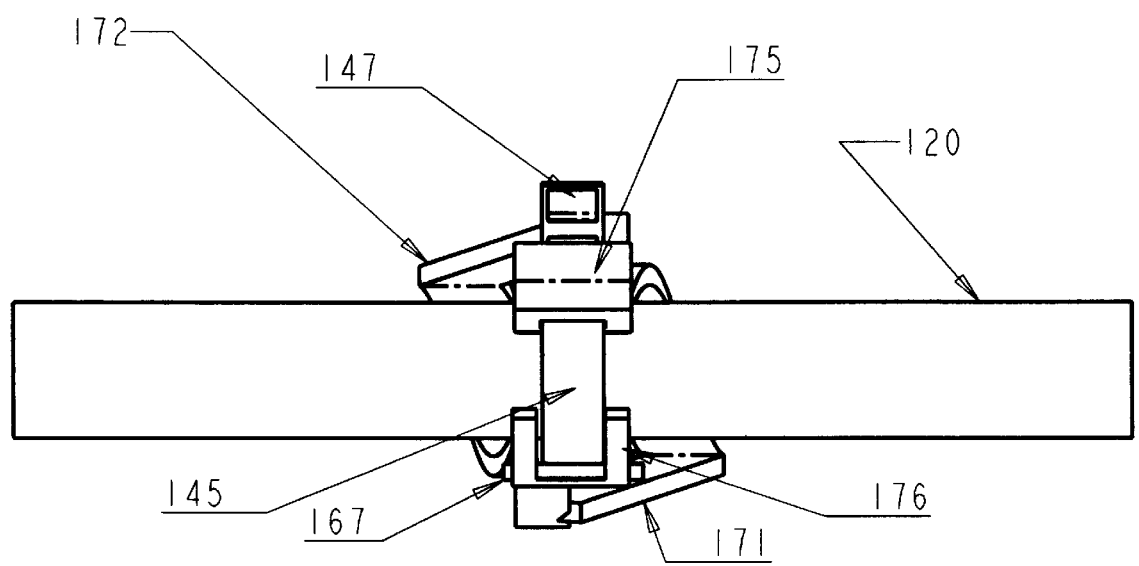
FIG. 1F is a frontal perspective view of the clip of FIG. 1A secured to a blood vessel demonstrating the vessel guard mechanism actuated.

FIG. 1F helps demonstrate how the distal portion of the vessel guard 145 acts as a fence to prevent the blood vessel 120 from slipping out of the clip.

The leaf-spring element 146 is optionally coated with a layer of magnetic material, such as magnetized iron. In such an embodiment the activation of a strong magnetic field, e.g., using an external electromagnet, will cause the leaf-spring element 146 to give way more easily to the force of the main spring 111, resulting in remotely actuated clip closure. If the bottom surface of the teeth, e.g., 149b is somewhat inclined, then a magnetic field with reverse polarity will cause the leaf spring to give way to the force of the blood vessel, causing remote re-opening and resetting of the clip.

The coil spring 111 is of such tension and bias that the clip can pinch shut a blood vessel of a fixed size (e.g., 3 millimeters diameters) with a low systolic blood pressure (e.g., less than 80 millimeters Mercury). The resilience of the leaf spring 146 is such that the vessel guard 145 can prop open the jaws of the clip so long as pressure within a blood vessel of a particular size to which it is applied is above a threshold level (e.g., 40 millimeters Mercury). When pressure within the blood vessel drops below the threshold, the force of the leaf spring 146 is no longer sufficient to keep the vessel guard 145 from slipping trough the vessel guard slot 144 and is overcome by the force of the main spring 111 resulting in closure of the clip.

All the embodiments described in this disclosure, except the seventh, rely on a resilient element 146 being overcome by the force of the main spring 111 when vessel 120 leakage occurs, resulting in clip closure. The embodiments also incorporate a mechanism to prevent the clip from re-opening on its own 149b. In each embodiment, the blood pressure below which automatic clip closure occurs approximately equals the difference between the force exerted by the main spring 111 on the vessel 120 and the force required to bend another resilient element (such as a leaf spring 146) sufficiently to disengage it from one of a number of wedge-shaped protrusions 147, 148, and 149.

In summary, the objective of this first embodiment is to stop flow in a blood vessel in response to leakage which results in bleeding. The detection mechanism in this case is the leaf spring 146 and the main spring 111, acting in opposition. The leaf spring 146 will yield to the main spring 111 in response to a drop in blood pressure and bend. This change in shape of the leaf spring 146 ultimately results in the clip closing. Hence, the leaf spring 146 and main spring 111 also serve as the actuator, and actuation of the clip is automatic in direct response to leakage from the blood vessel.

One can manufacture the invention by modifying an existing alpha, pivot, or mobile-fulcrum clip using the following procedure:

(1) Shorten one jaw (known as the "bottom jaw") 176 by the intended height of the distal element of the vessel guard 145; for example, by ⅓ the length of the jaw.;

(2) Create a trough 164 in the bottom jaw of length roughly one to three times the diameter of the vessel for which the clip is intended; this length will also be the length of the proximal element of the vessel guard 145;

(3) Using the same material as the original clip, create the vessel guard of width roughly 90% the width of the jaws.

A method for using the invention for intracranial aneurysm surgery is described as follows. Briefly, after the surgical opening has been completed, as blood vessels proximal to and distal to the aneurysm are identified, a clip is applied to those vessels which can potentially participate in hemorrhage. Should the aneurysm rupture prior to its repair, the clips will help arrest bleeding so that the surgeon can see where vessel repair is necessary. When any necessary vessel repair is performed, each clip may be reset to the open position or removed.

To reiterate, the preferred embodiment of the invention comprises four main configurations. The first configuration is a transition configuration illustrated in FIG. 1B, where the invention is being applied to a blood vessel 120. In the second configuration (shown in FIG. 1C), the blood vessel 120 is secure within the jaw hold, and the jaws are held open by the vessel guard 143 acting on the leaf spring in the opposing jaw 171. The third configuration, illustrated in FIGS. 1D and 1E, comprises automatic or remote actuation of clip closure, e.g. in response to hemorrhage or in response to a transient magnetic field; in this case, the leaf spring 146 bends and is no longer capable of blocking passage of the vessel guard. The final configuration is that of complete clip closure, resulting in blockage of flow within the blood vessel.

An additional aspect of the invention is the feature of remote clip actuation. During aneurysm surgery it may be desirable to limit blood flow to the aneurysm so that the aneurysm may be explored more safely. In such cases, temporary clipping of vessels proximal and distal to the aneurysm is performed in the absence of acute hemorrhage. The risk of temporary clipping includes stroke since vital areas of the brain are deprived of blood flow during the temporary clipping. For this reason, the surgeon must work expeditiously during the temporary clipping. If the surgeon has placed clips of the type described by this invention, then he may work on the aneurysm without actually clipping shut the blood vessels proximal and distal to the aneurysm; these vessels will be clamped shut only when acute hemorrhage occurs. If the surgeon does not want to risk even minimal hemorrhage, he can actuate the clip remotely. If the resilient element 146 depicted in FIG. 1D is magnetic or ferromagnetic, then, while the clip is secured to the vessel a switch-activated solenoid external to the patient can be used to generate a magnetic field to exert a force on the leaf spring 146 sufficient to cause closure of the clip in absence of hemorrhage. In contrast to prior art, this method for remote activation of surgical clips does not comprise a direct physical coupling between the clip and the actuating device.

It should be noted that a magnetic field can also be used to actuate remote resetting of the clip. In this case, after the clip has been actuated and is pinching shut a vessel, a magnetic field of sufficient strength can be employed for a brief period of time so that the leaf spring will move toward the vessel-bearing surface of the jaw in which it lies, thereby permitting the protrusions 148, 149 on the vessel guard to travel toward the vessel-bearing surface of the opposing jaw and permitting ordinary blood pressure within the vessel to separate the jaws of the clip; once the jaws are open the magnetic field may be shut off, and the clip should remain open so long as the jaws are sufficiently open and the blood pressure is sufficient as well.

The preferred embodiment of the invention also permits direct manual actuation of the clip. If the surgeon wishes to directly manually actuate the clip, this may be done by gently pinching the blood vessel or other conduit in the neighborhood of the clip; this will result in a reduced blood pressure within the clip and, if sufficient, will trigger its closure.

Such a method is useful for clipping the neck of aneurysms as well. Often after an aneurysm clip is placed on the neck of an aneurysm, it must be re-adjusted a few times to assure safe placement. Such re-adjustment necessarily risks rupture of the aneurysm since the blood vessel wall is at risk for damage from each clip placement. By using the present invention, the surgeon can pre-position the clip around the neck of an aneurysm without having to clip the neck until the clip configuration is verified to be safe. At that point, the surgeon simply pinches off blood flow proximal and/or distal to the aneurysm neck to actuate clip closure.

Figure 2:
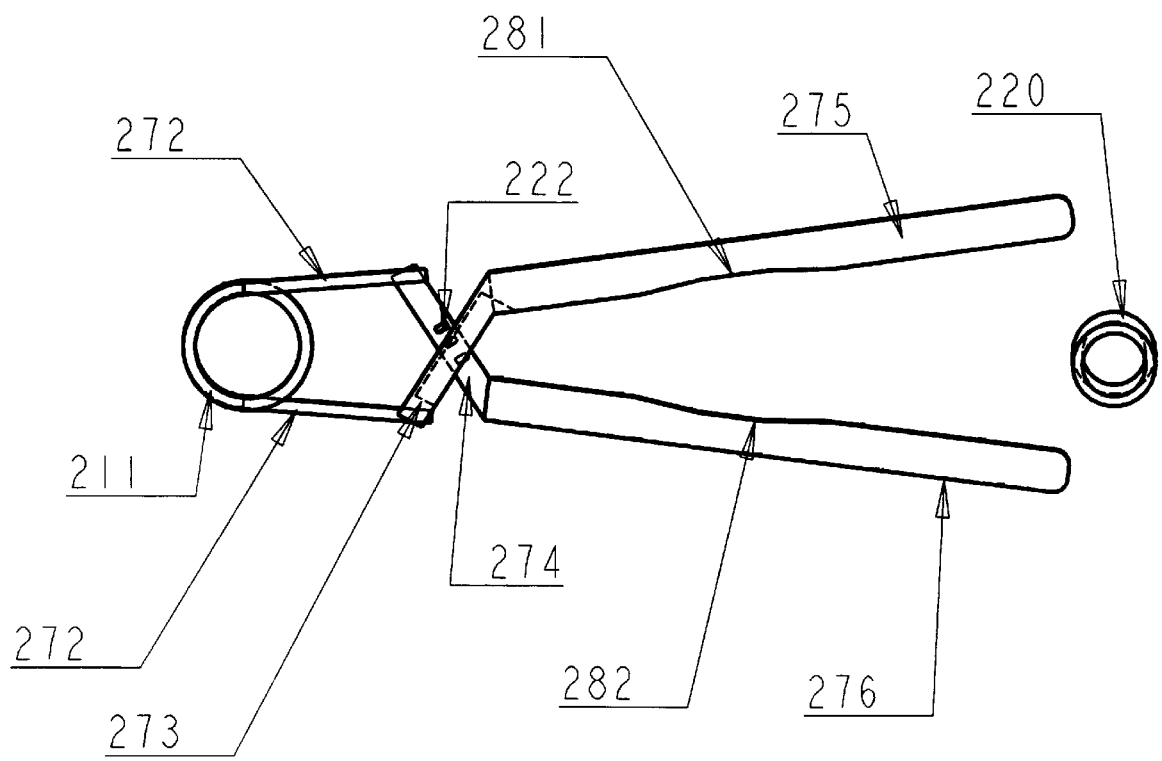
FIG. 2A is a side view of an alternate embodiment of the invention which employs an array of wedge-shaped protrusions on the crossover of the lower jaw to control flow based on the force needed by the crossover of the upper jaw to skip over the next-in-line protrusion on the crossover of the lower jaw.
FIG. 2B is a detailed side view of the clip of FIG. 2A showing the flow-modulating mechanism while the clip is in transition to a stable open state.
FIG. 2C is a detailed side view of the clip of FIG. 2A showing the flow-modulating mechanism while the clip is in a stable open state.
FIG. 2D is a detailed view of the crossover area of the clip of FIG. 2A illustrating the series of wedge-shaped protrusions on the lower crossover.
FIG. 2E is another detailed side view of the clip of FIG. 2A illustrating a cross-section of the flow-modulating mechanism.
FIG. 2F is a top view of the clip of FIG. 2A showing in detail the crossover area, with the wedge-shaped protrusions being visible between the crossovers.

FIGS. 2A, 2B, 2C, 2D, 2E, and 2F illustrate a second embodiment of the invention. Here, jaw closure is modulated with the aid of protrusions 222, 223, and 224 situated on crossover 274. These protrusions 222, 223, and 224 serve as abutments to the opposing crossover 273. FIGS. 2B and 2C illustrate the crossover in transition to a stable position, held by the protrusion 224. FIG. 2C illustrates how the protrusion 224 is stopping the crossover 273 from moving to a closed position. The crossover 273 has a trough cut out 221 which results in a thin remaining overhang 273a to interact with the protrusions 222, 223, and 224 in the manner of a limited-load detent. The force exerted by the protrusion 224 to oppose the closure force exerted by the main spring 211 is only effective if the blood vessel 220 has a normal intravascular pressure. Should the vessel 220 bleed, the protrusion 224 will no longer be able to hold back movement of the crossover 273, and the crossover 273 will skip over the protrusion 224 to bypass it; this skipping is possible because the main spring 211, by its helical nature, allows the jaws to scissor in and out of the plane of view seen in FIG. 2B.

FIGS. 2A, 2B, and 2C also demonstrate the concavities 281, 282 on both of the jaws 275, 276 which help secure the blood vessel 220 to the clip.

Figure 2D:
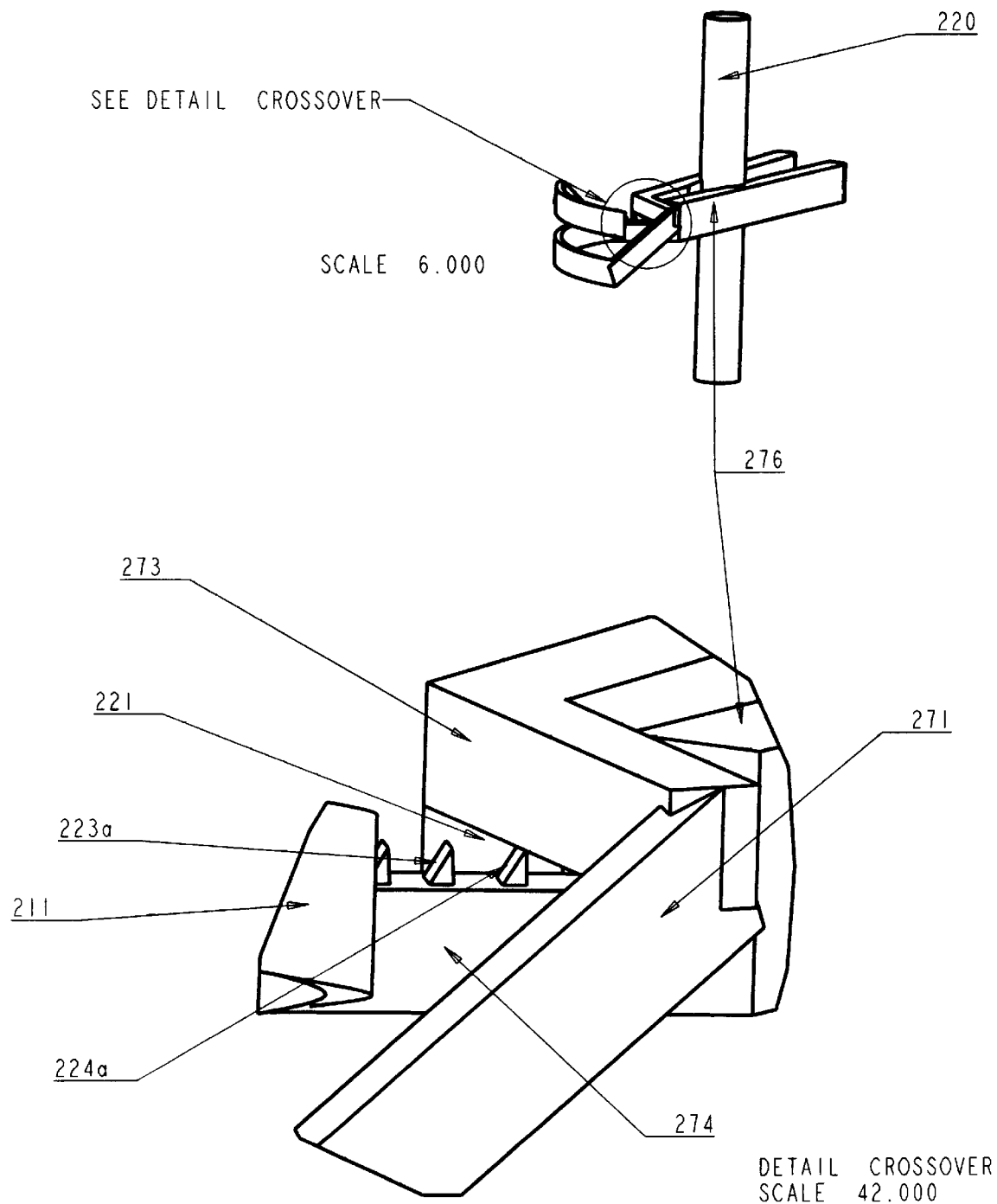
Figure 2E:
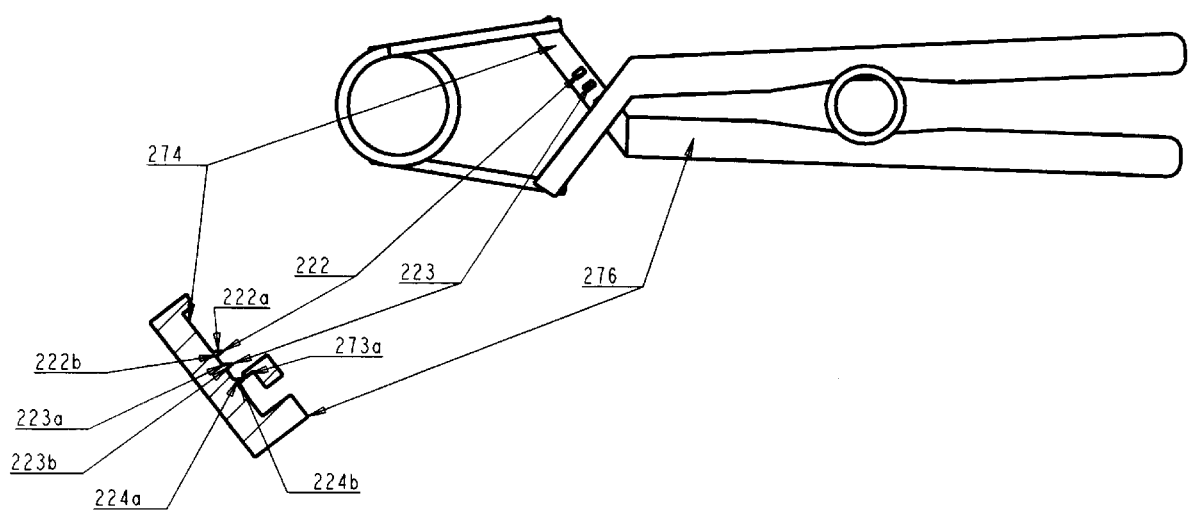
Figure 2:
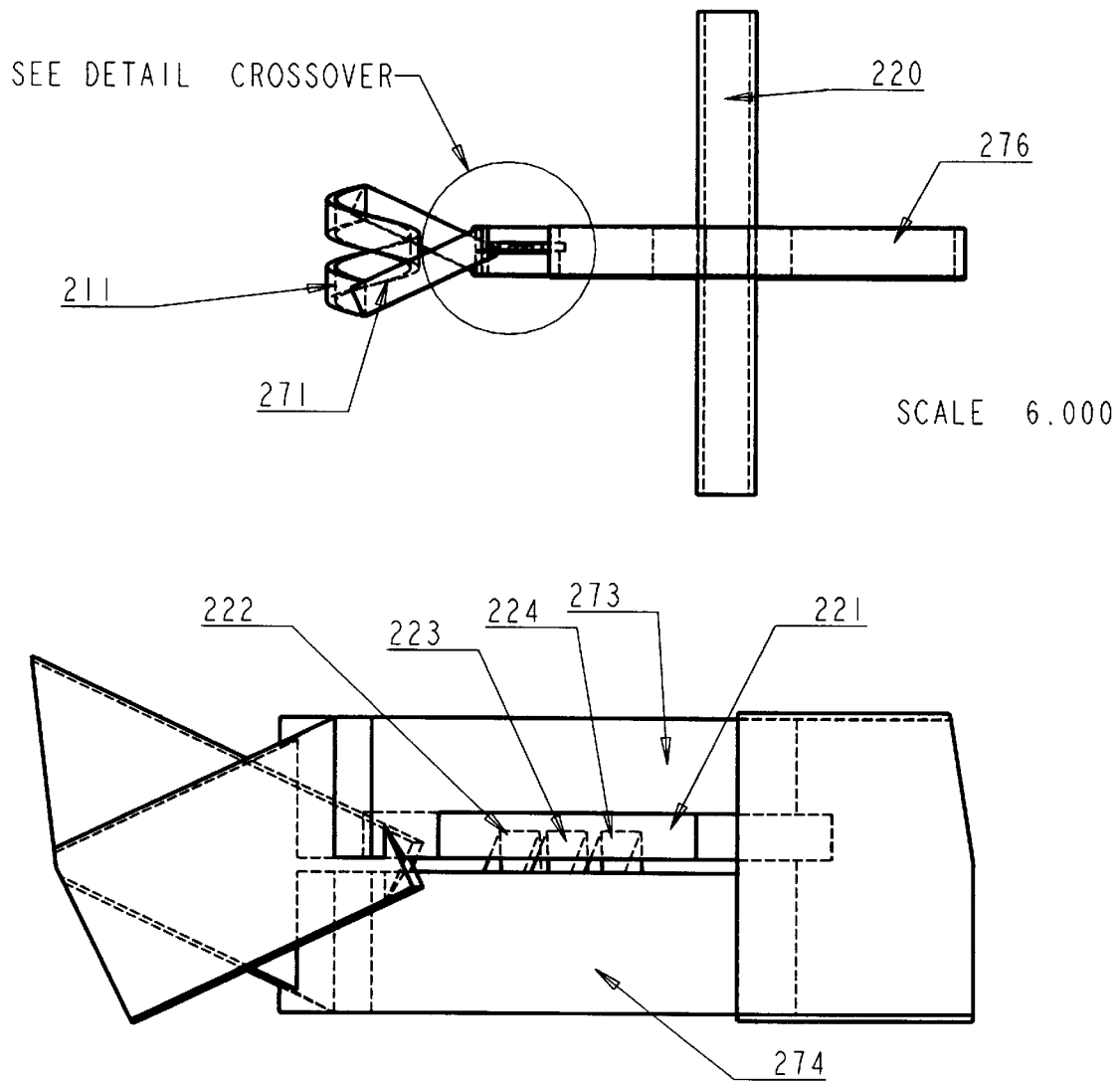
Figure 3A:
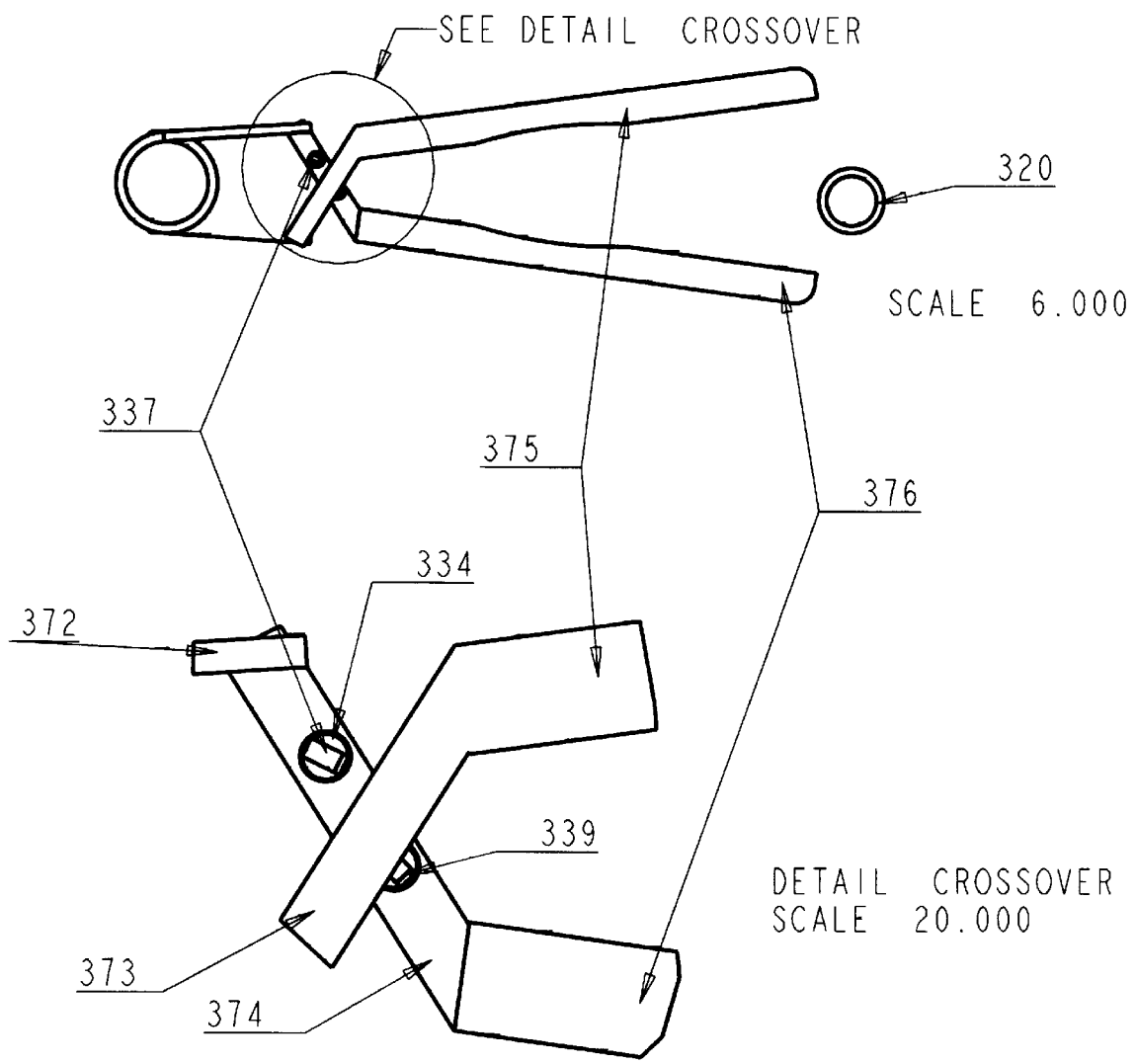
FIG. 3A illustrates a third embodiment of the invention in which protrusions on the lower jaw's crossover are positioned on a depressible base which is supported by a compression spring.
Figure 3B:
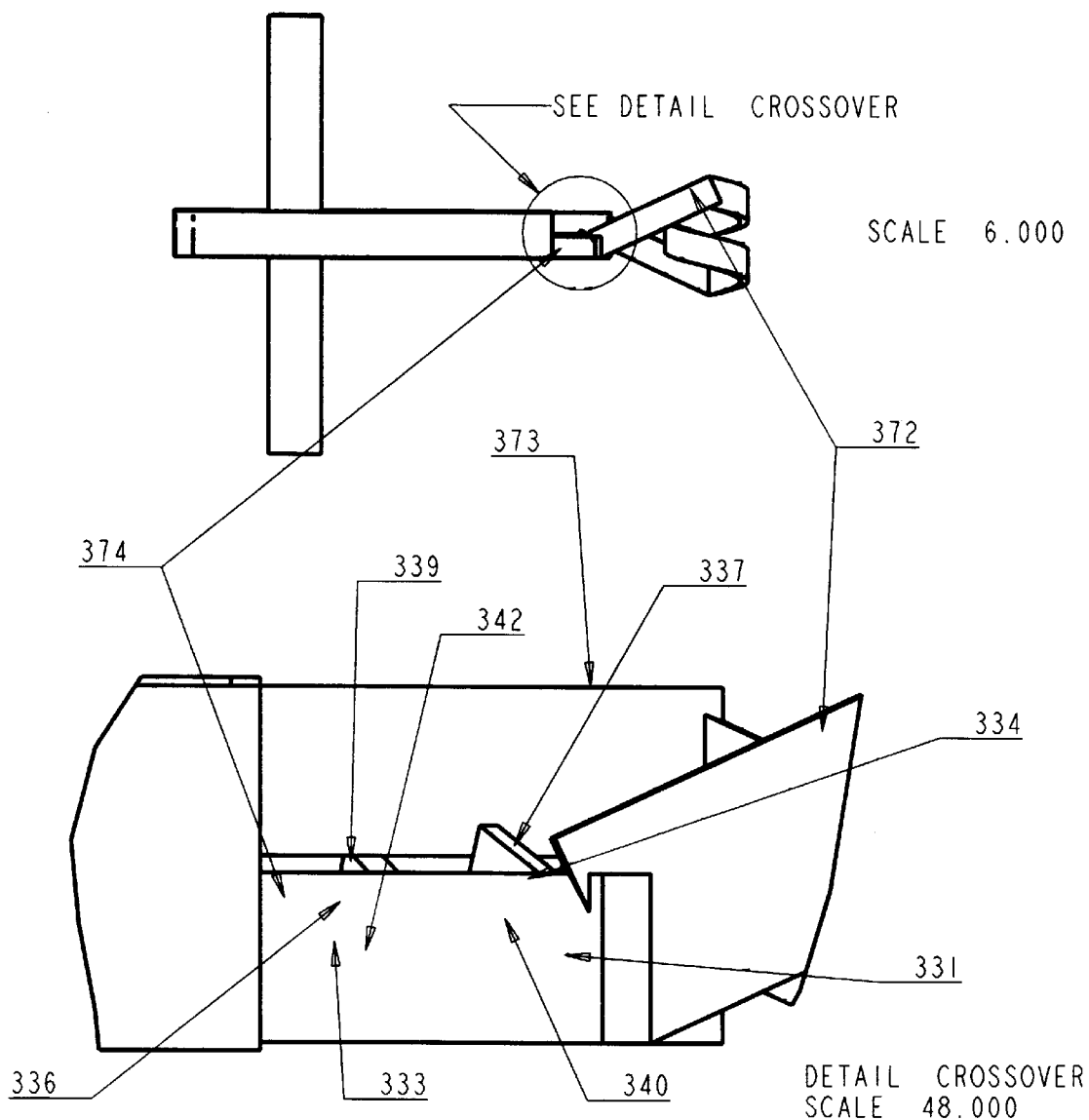
FIG. 3B illustrates a detailed view of the crossover region of the clip of FIG. 3A from the top.
Figure 3D:
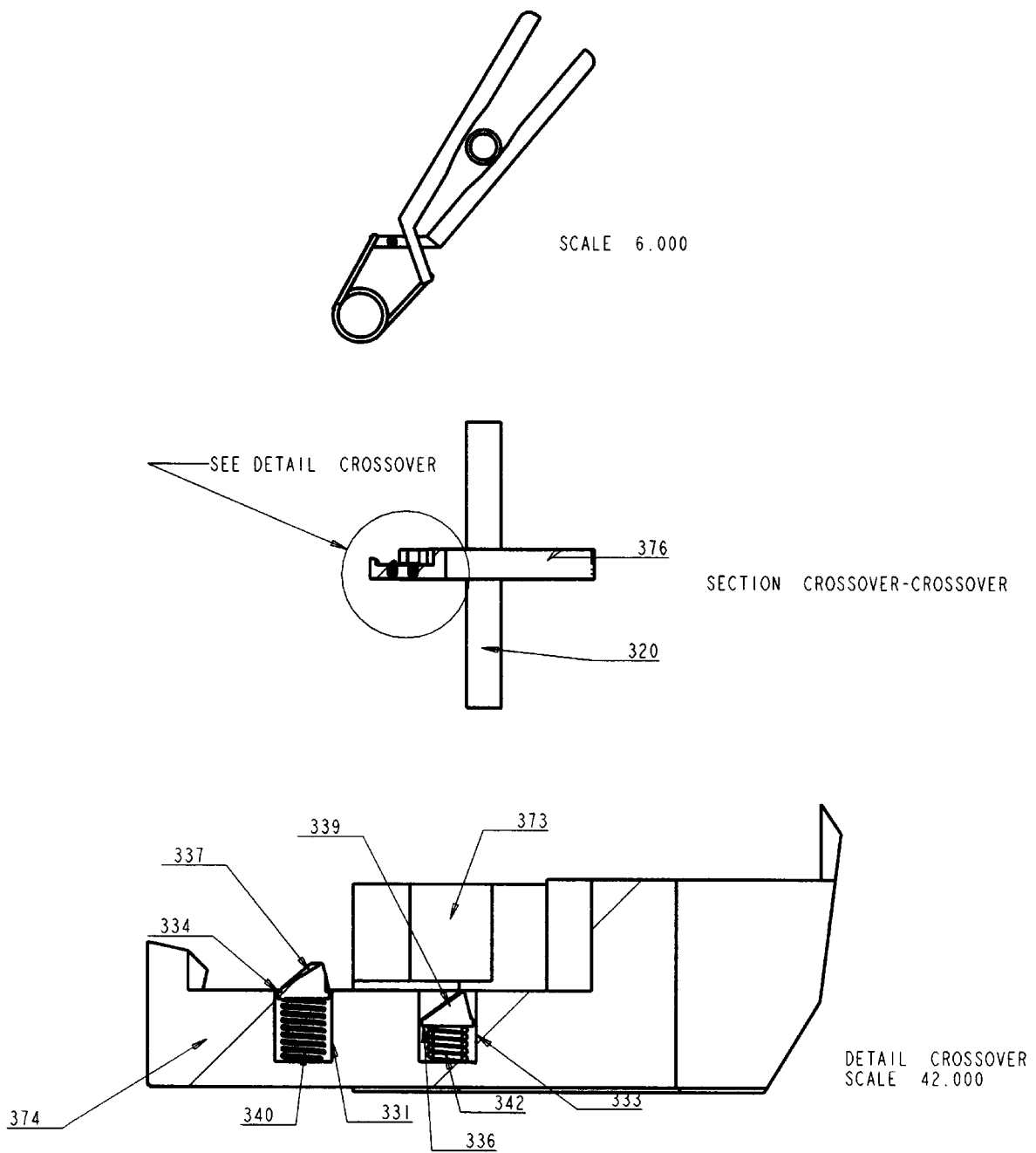
FIG. 3D is a cross-sectional detail view of the crossover area of the jaws of the clip of FIG. 3A, illustrating the depressible buttons which serve to modulate clip closure.

As seen in FIGS. 2D and 2E, the protrusions 222, 223, 224 are wedge shaped so that their proximal surfaces 222a, 223a, 224a are inclined and their distal surfaces 222b, 223b, 224b are nearly perpendicular to the crossover 274. This adds a preferred direction to the detent mechanism so that once the clip is actuated, self-reopening will not occur even if blood pressure proximal and/or distal to the vessel is re-established.

FIGS. 3A, 3B, 3C, and 3D illustrate a third embodiment of the invention. In this embodiment, once again an array of protrusions 337, 339 on the crossover 374 help modulate clip closure. However, in this case, each protrusion 337, 339 is depressible within cylindrical sockets 331, 333 in the crossover 374. As particularly shown in detail in FIG. 3D, the protrusions are wedge-shaped buttons 337, 339, each of which is fixed upon a circular disc 334, 336; each disc in turn sits atop a compression coil spring 340, 342 lying within the sockets 331, 333. The spring constant of each spring 340, 342 is such that the buttons 337, 339 will be depressed by the overriding crossover 373 when pressure within the blood vessel 320 drops due to sudden hemorrhage. Hence, the springs 340, 342 resist closure of the clip when the vessel 320 has a normal blood pressure. Once again, slippage is prevented by concavities 381, 382 (FIG. 3C) on each of the pinching surfaces of the jaws 375, 376; in addition, the surfaces may be ridged or lined with a gripping material such as rubber to help keep the vessel in place while the clip remains open.

Figure 4A:
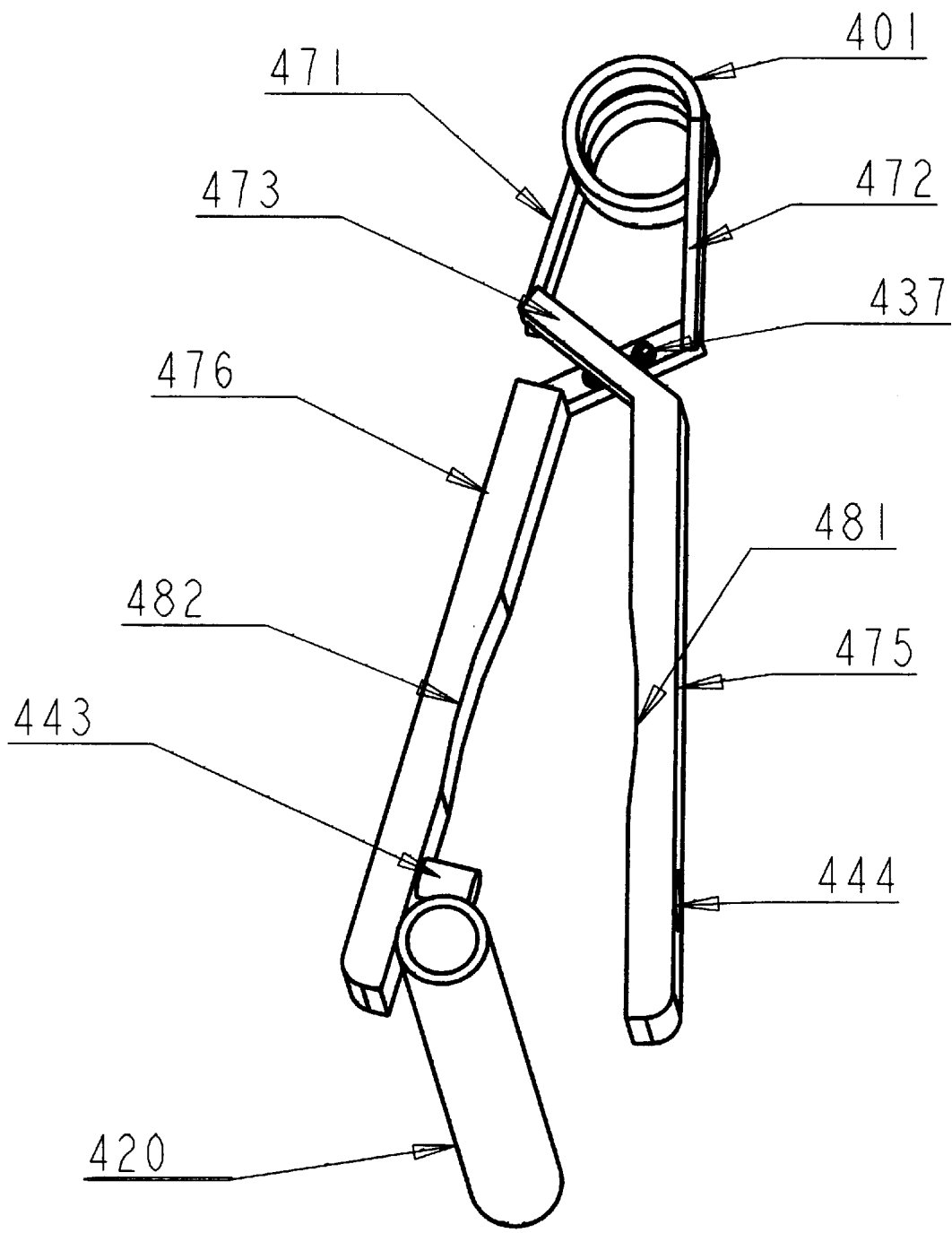
FIG. 4A is a perspective view of a fourth embodiment of the invention in which a protrusion is provided at the end of one of the jaws to help prevent slippage of the clip once secured to a vessel.
Figure 4B:
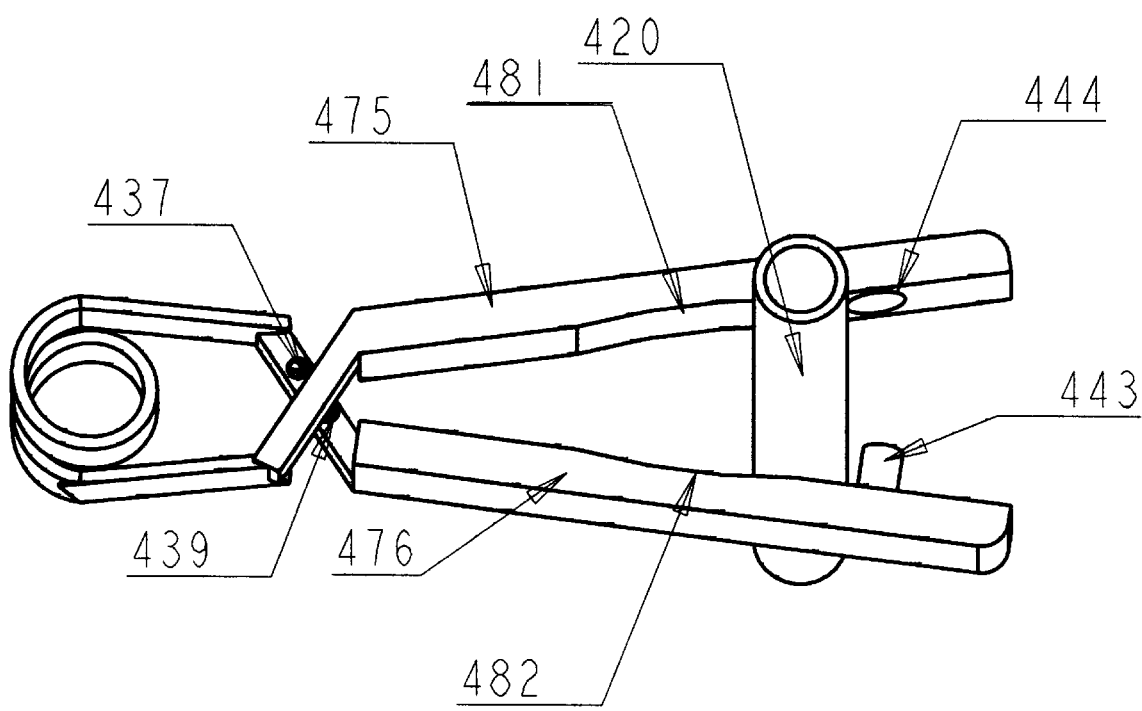
FIG. 4B is a perspective view of the clip of FIG. 4A being applied to a vessel.
Figure 4:
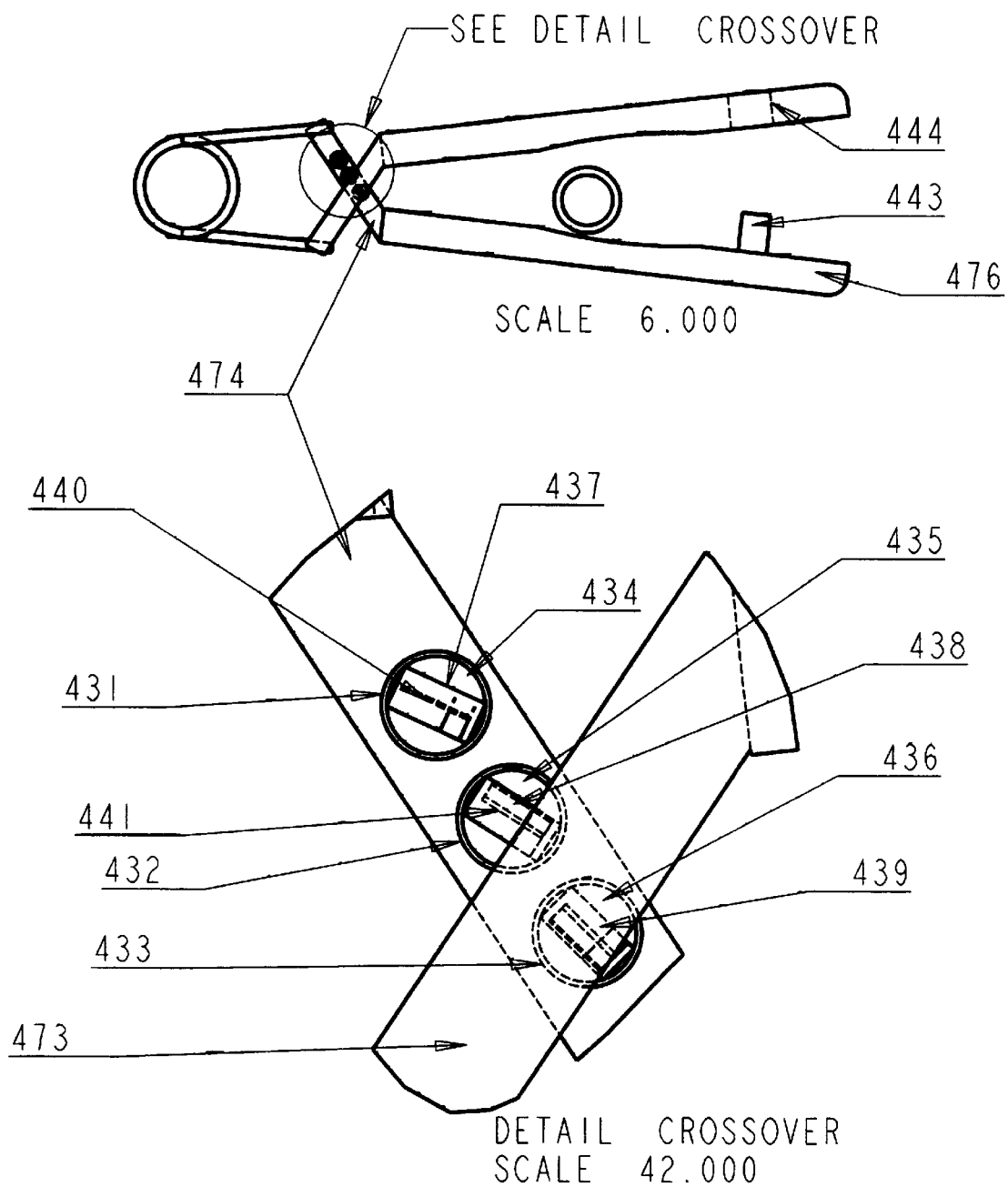
FIG. 4C is a detailed view of the crossover region of the jaws of the clip of FIG. 4A.
FIG. 4D illustrates, by way of cross-sectional detailed view, the use of vertically oriented leaf springs rather than coil springs to support the base of the jaw-closure-modulating buttons.
FIG. 4E is a cross-sectional view of the crossover region of the jaws which demonstrates the resilience and disparate orientations of the vertical leaf springs.

A fourth embodiment of the invention is illustrated in FIGS. 4A, 4B, 4C, 4D, and 4E. This embodiment employs depressible protrusions 437, 438, 439 as in the third embodiment. However, as seen in FIGS. 4A and 4B, an additional element is introduced to further prevent slippage of the vessel from the clip; namely, a protrusion 443 on the inner surface of one of the jaws 476 which acts as a fence; when the clip is closed, the protrusion 443 fits into a mating slot 444 within the opposing jaw 475.

Figure 4E:
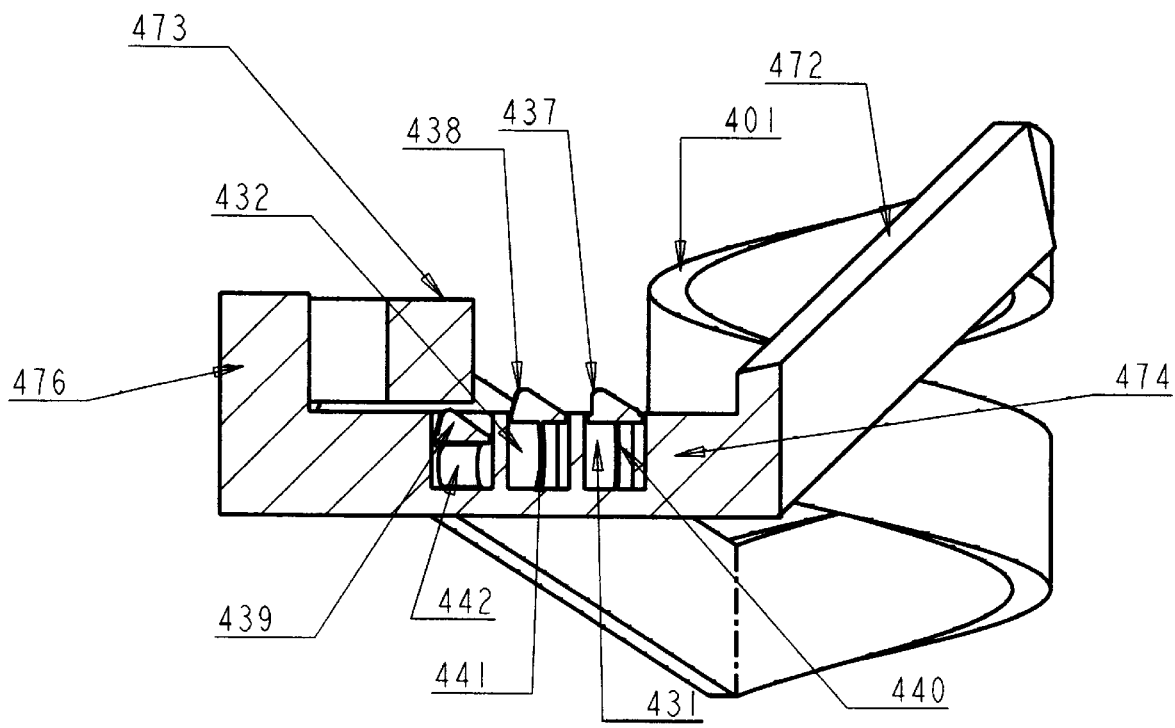

FIGS. 4C and 4D illustrate that in this fourth embodiment the resilient elements upon which the buttons 437, 438, 439 lie are vertical leaf springs 440, 441, 442. FIG. 4E illustrates how the leaf springs have disparate orientations and how the overriding crossover 473 depresses the button 439 to bend the leaf spring 442. By coating the middle portion of the surfaces of each leaf spring 440, 441, 442 with a ferromagnetic or magnetic material, a sufficiently strong magnetic or electromagnetic field can remotely trigger automatic clip closure by bending the leaf springs 440, 441, 442 and weakening their efforts to keep the crossover 473 from depressing their corresponding buttons 437, 438, 439.

Figure 5A:
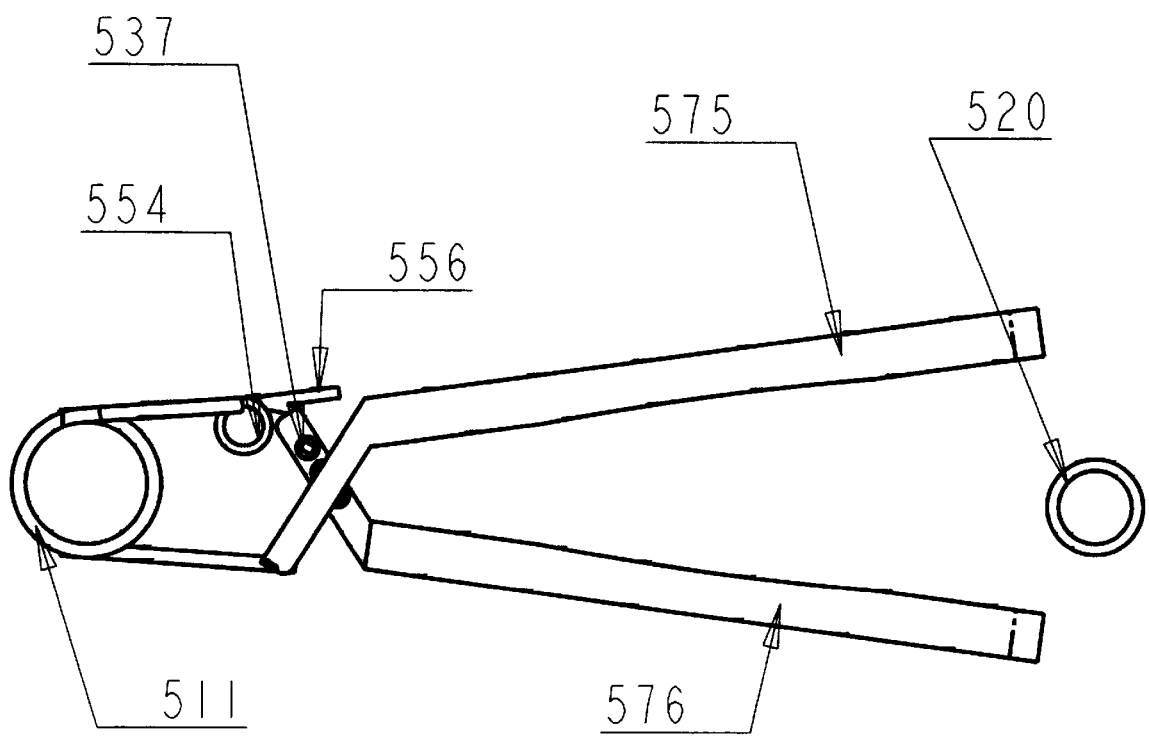
FIG. 5A is a side view of a fifth embodiment of the invention which employs a secondary spring mechanism to join one arm of the clip to its corresponding jaw thereby reducing the space between the distal ends of the jaws when the clip is closing and consequently reducing the risk of slippage.
Figure 5B:
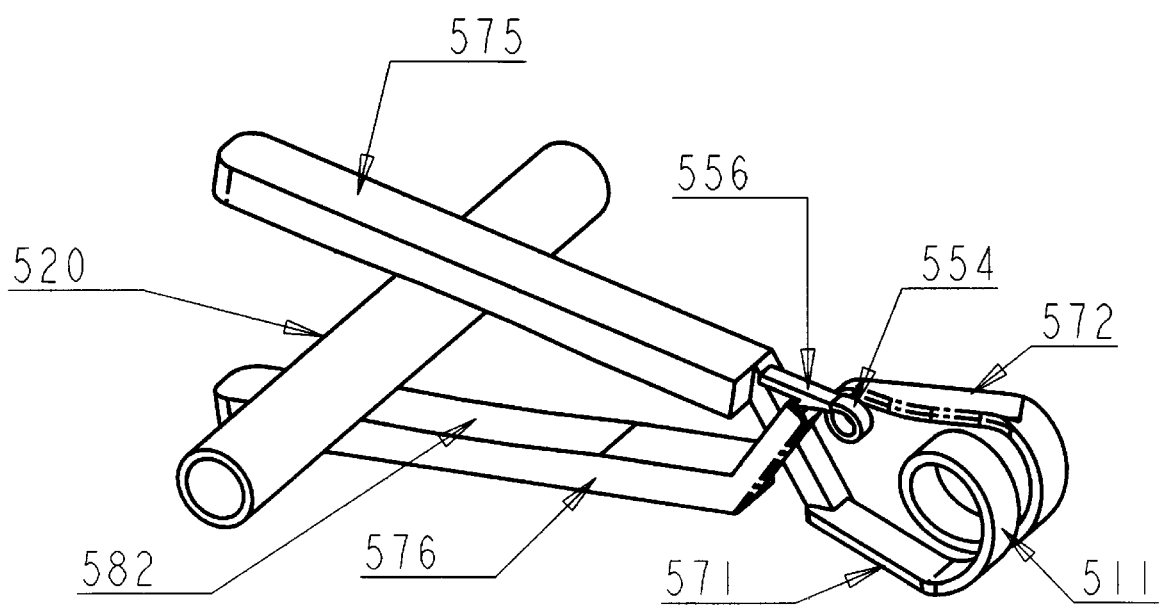
FIG. 5B is a perspective view of the clip of FIG. 5A which illustrates the jaws in open position surrounding a blood vessel.
Figure 5C:
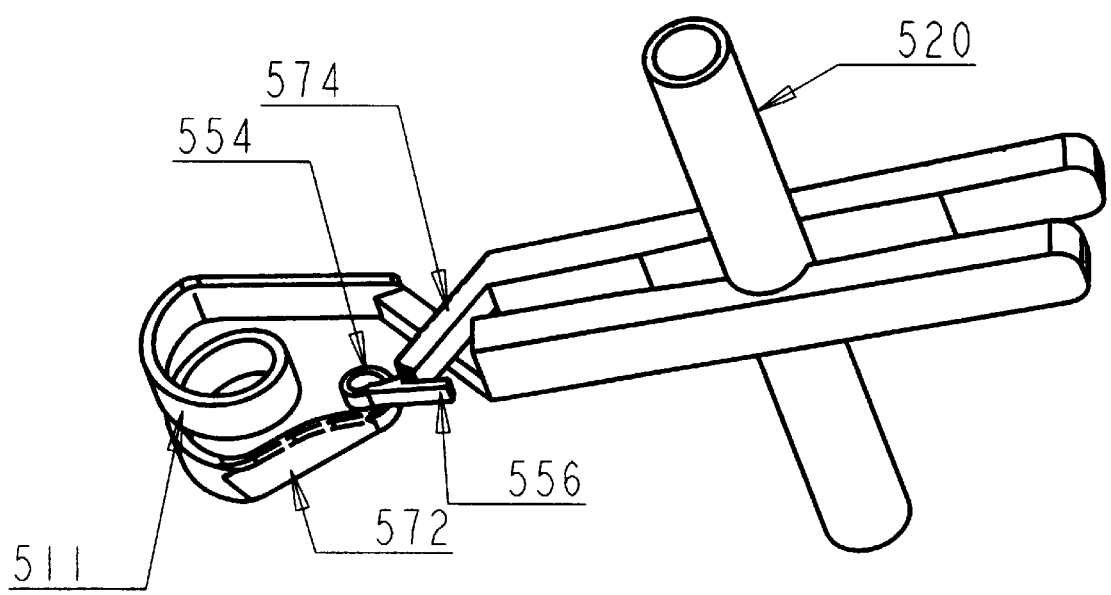
FIG. 5C is another perspective view of the clip of FIG. 5A which illustrates the jaws closing over the vessel.
Figure 5D:
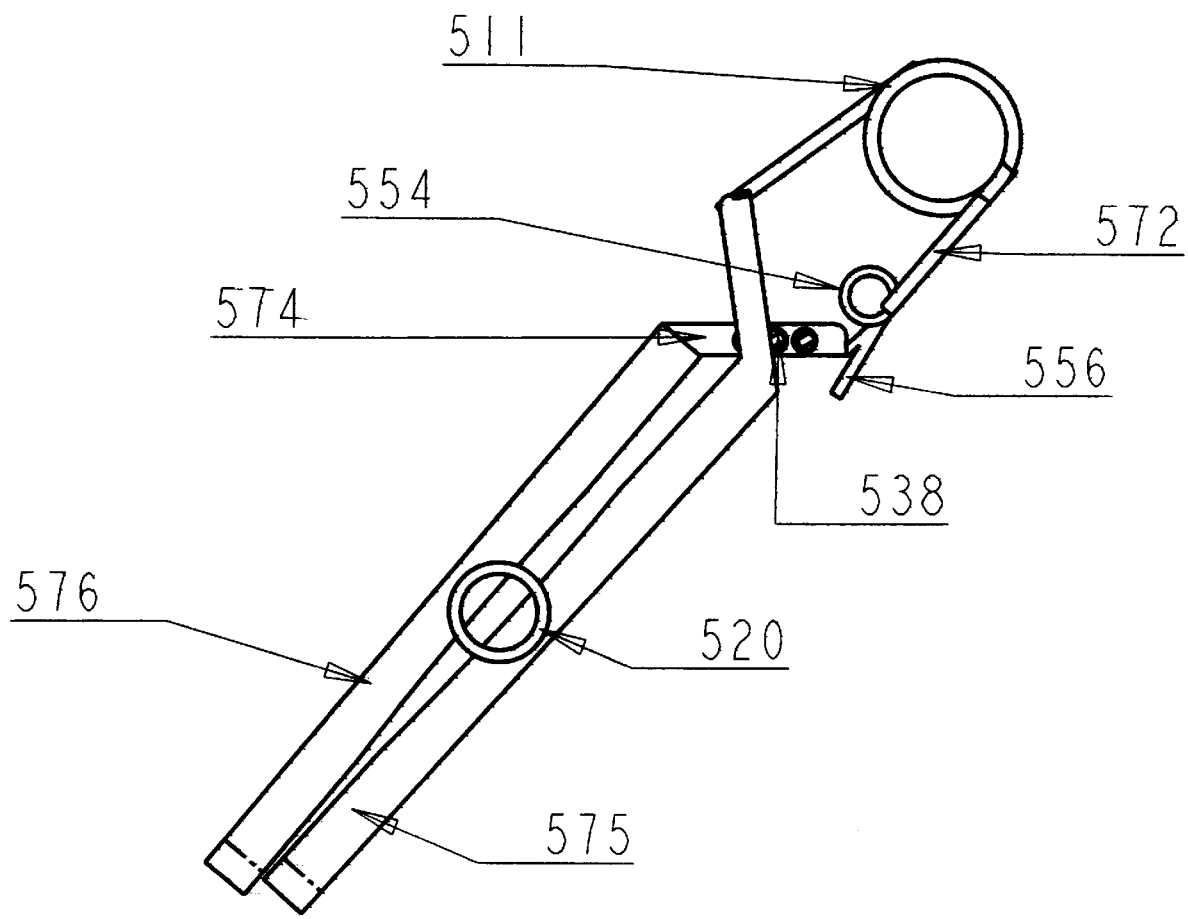
FIG. 5D is a side view of the clip of FIG. 5A with the jaws in a closed position.

FIGS. 5A, 5B, 5C, and 5D illustrate a fifth embodiment of the invention. In this embodiment depressible buttons 537, 538 are once again employed to modulate clip closure. However, a new mechanism 554 to prevent slippage of the blood vessel 520 is introduced. It is seen in FIG. 5A that with the clip in an open position the gap distance between the distal surfaces of the jaws 575, 576 is greater than the gap distance between the proximal surfaces of the jaws 575, 576; this wideness at the distal end of the clip is necessary to initially embrace a blood vessel with the clip. However, once the blood vessel has entered the jaws of the clip, it is preferable to keep the distal gap distance small relative to the proximal gap distance so that any translational force exerted by the clip on the vessel 520 is directed proximally rather than distally with a consequent reduced risk of the vessel slipping out of the clip. To accomplish this narrowing of the distal gap distance when the vessel is within the clip, a joint is created between one arm 572 (FIG. 5B) and its corresponding jaw 576. A helical spring 554 is biased to bring the bottom jaw 576 closer to upper jaw 575, and governs the joint between arm 572 and jaw 576. A forward extension 556 is present so that a clip applier can approximate this extension 556 to the opposite arm 571 and thereby make the distal gap distance wide enough for initial entry of the vessel within the jaws of the clip 575, 576; once the clip applier is removed, the spring 554 will move to its natural bias and narrow the distal gap between the jaws 575, 576. FIG. 5D illustrates how, when closed, the clip has a narrower gap distance distal than proximal with a consequent inward translation force on the vessel 520 should the vessel slip from the gripping surfaces of the jaws 575, 576.

Figure 6A:
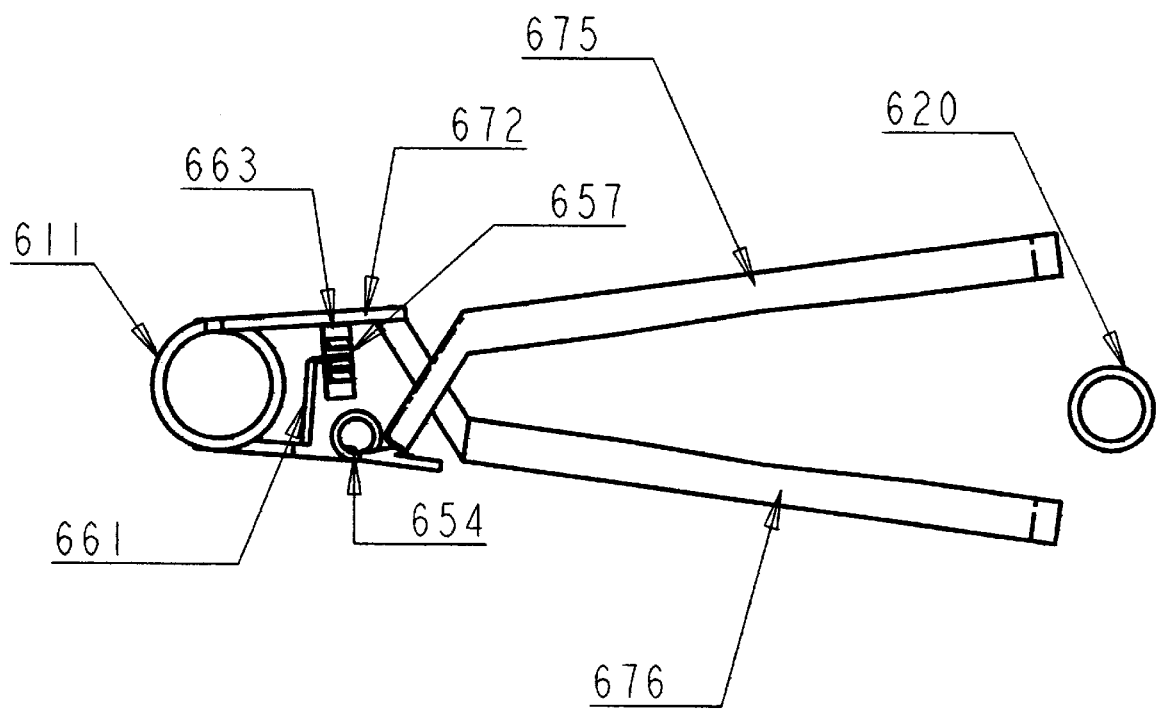
FIG. 6A is a side view of a sixth embodiment of the invention which employs a closure-modulating mechanism based at the arms of the clip.
Figure 6B:
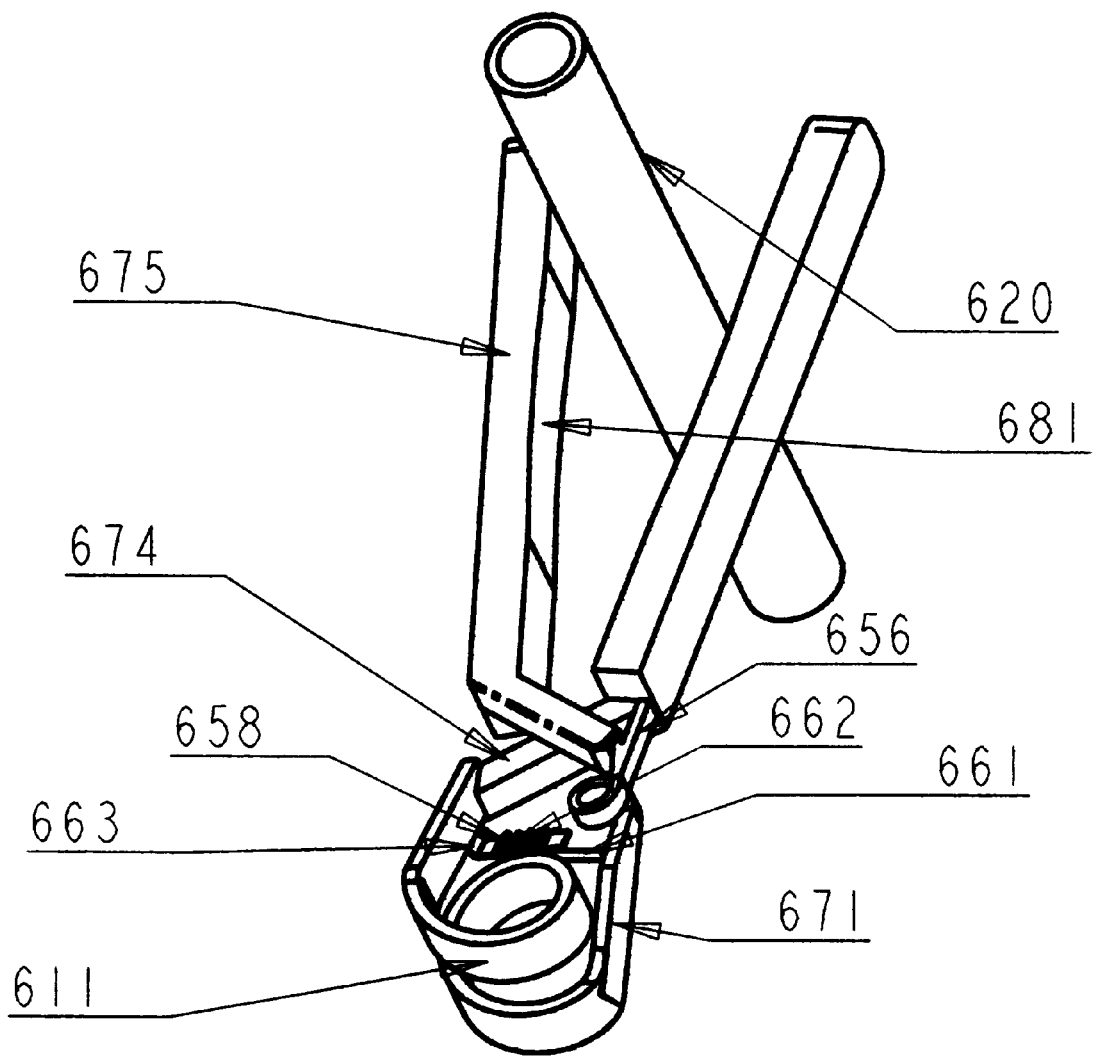
FIG. 6B is a perspective view of the clip of FIG. 6A which illustrates a protrusion-bearing leaf spring extending internally from one of the arms of the clip and a rod extending internally from the opposing arm.
Figure 6C:
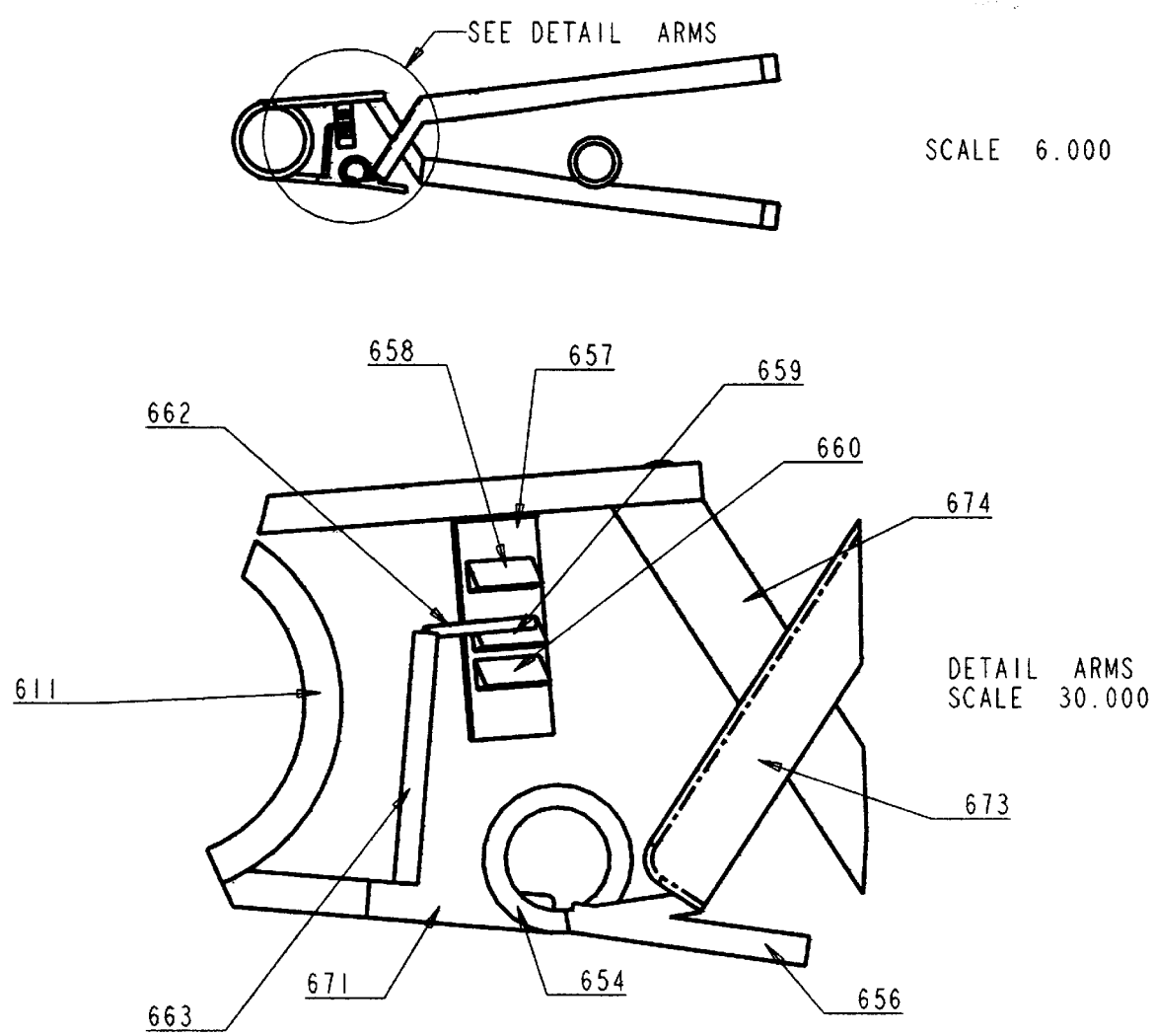
FIG. 6C is a detailed view of the arms of the clip of FIG. 6A depicting a leaf-spring mechanism which modulates jaw closure.

A sixth embodiment of the invention is illustrated in FIGS. 6A, 6B, 6C, and 6D. This embodiment features a leaf spring control mechanism located on the arms 671, 672 of the clip. As shown in FIG. 6C, a rigid base 657 extends from one arm 672 toward the opposite arm 671. On the surface of the base 657 is an array of wedge-shaped protrusions or "teeth" 658, 659, 660. From the opposing arm 671 emerges a rigid rod-like element 661 at the end of which is a rigid hook element 662 which interacts with the teeth 658, 659, 660.

Figure 6D:
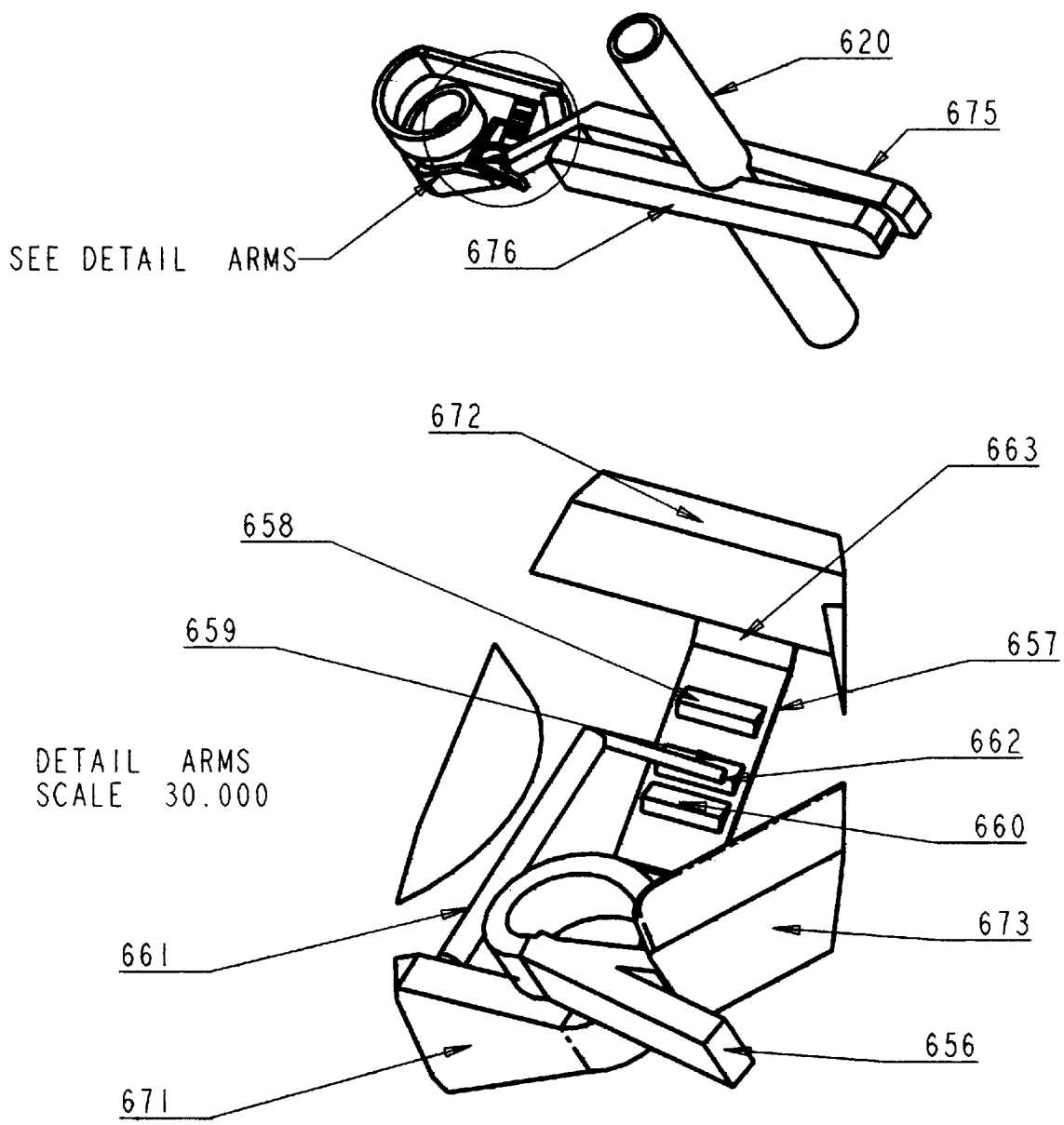
FIG. 6D is another detailed perspective view of the arms of the clip of FIG. 6A which illustrates the rod-hook element skipping over the intermediate protrusion of the leaf spring.

FIG. 6D illustrates the leaf spring attachment 663 of the base 657 to the arm 672. The resilient element 663 is biased to keep the base parallel to the side surface of arm 672. Resilience of the leaf spring 663 causes the rod-hook-base mechanism to function as a force-limited detent, preventing closure of the clip so long as the force exerted by the leaf spring 663 is augmented by the force exerted by the blood vessel 620 on the jaws 675, 676. Also, if the base element 657 is magnetic, then an external transiently actuated magnetic field can be used to reduce or augment the effective resilience of the leaf spring 663, thereby permitting remote modulation of clip closure. Notice that the protrusions 658, 659, 660 on the base 657 are shaped so as to prevent self-reopening of the clip, once closed.

A seventh embodiment of the invention is illustrated in FIGS. 7A, 7B, 7C, 7D, and 7E. In this embodiment, the main spring 711 serves both to close the clip and to sense leakage from the vessel 720. The buttons 737, 738, 739 (FIG. 7D) are mounted on springs with a low spring constant so that the buttons are easily depressible. The function of the buttons 737, 738, 739 in this embodiment is to lock the clip in its closed state, once it closes.

The distal portion 743 of the a hinged mechanism 745 serves to guard the blood vessel 720 from slippage and fits within a slot 744 within the opposing jaw 775.

In this embodiment, the tension exerted by the main spring 711 is at a low level so that it will only pinch shut a vessel with a low pressure; e.g., the closing tension of the main spring is about 40 mm Hg. Hence, if the vessel 720 bleeds and drops its pressure to less than 40 mm Hg., the clip will close. As shown in FIG. 7E, the button 739 keeps the clip closed until re-opened by the surgeon.

Figure 7A:
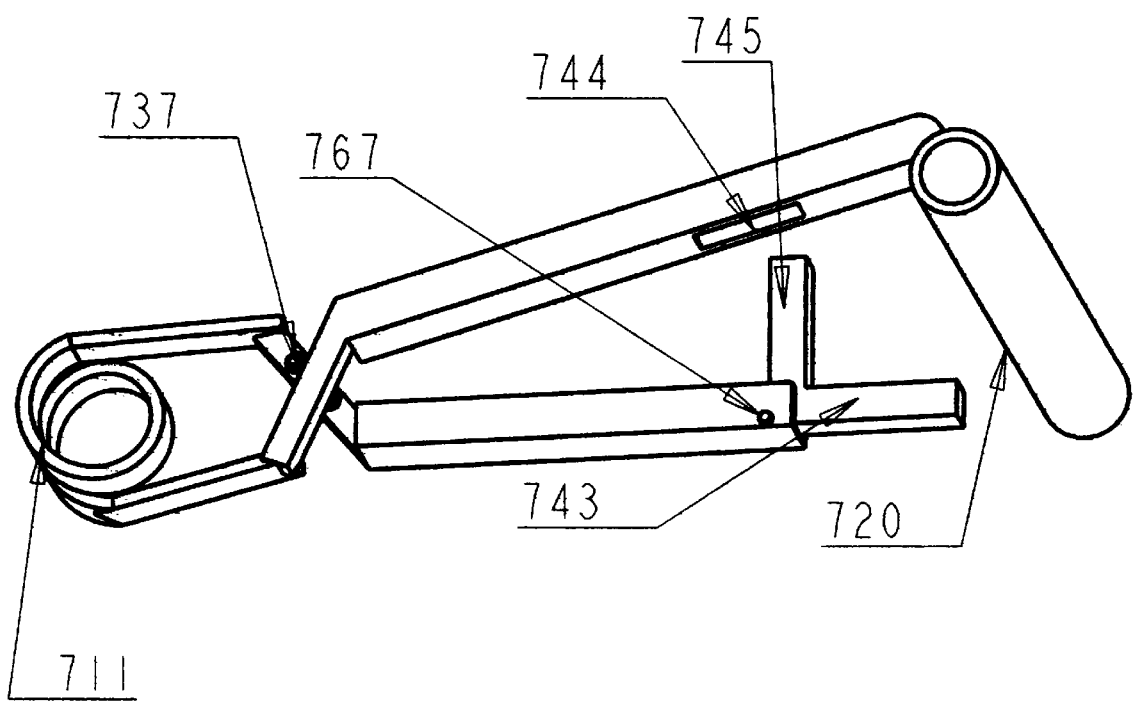
FIG. 7A is a perspective view of a seventh embodiment of the invention which employs a low-tension main spring combined with a hinged vessel guard at the tip of one of the jaws to modulate flow, and buttons on the crossover function serving to lock the clip closed, when closed, until re-opened by the surgeon.
Figure 7B:
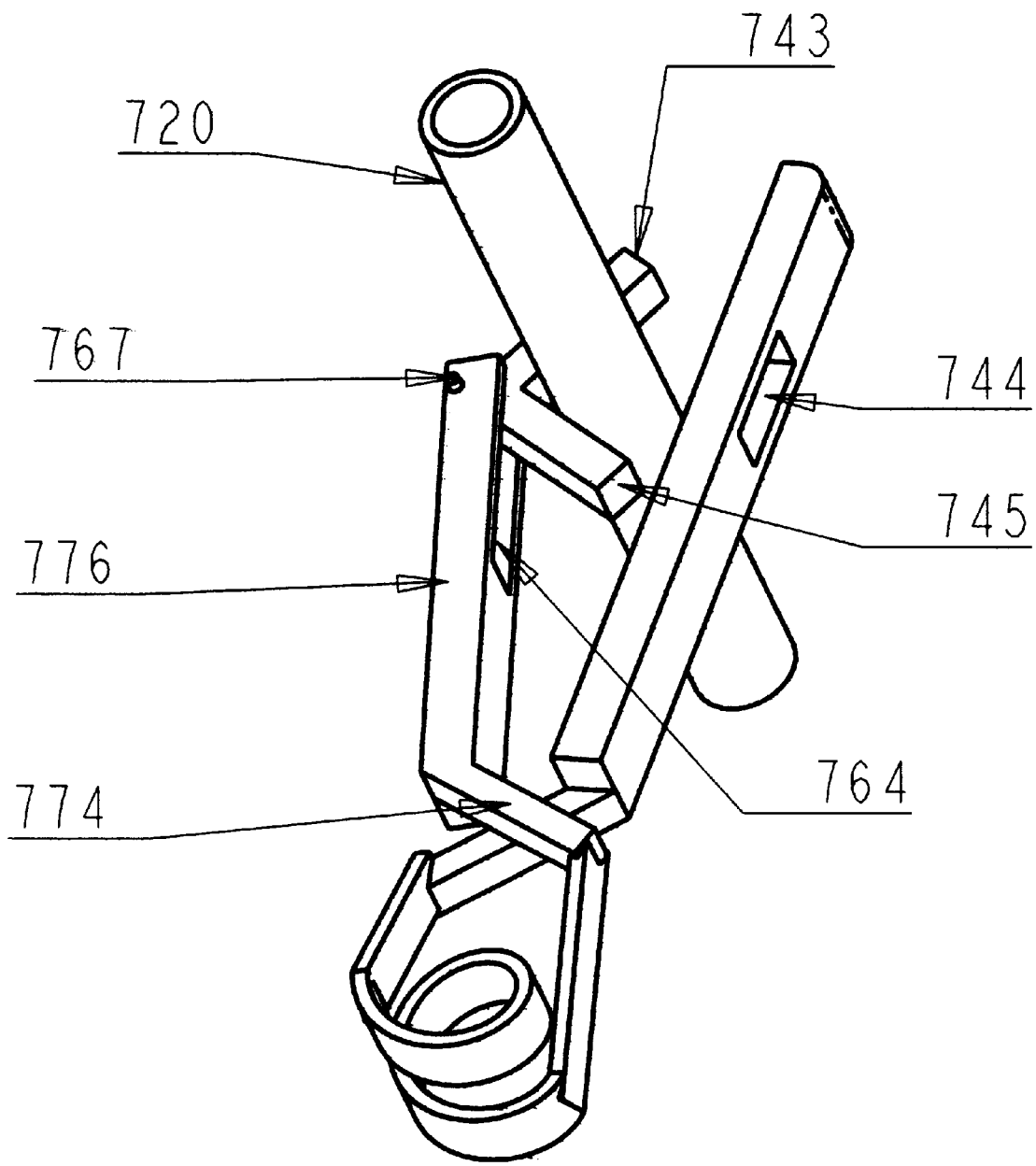
FIG. 7B is a second perspective view of the clip of FIG. 7A showing the actuation of the jaw guard as the clip is applied to a blood vessel.
Figure 7C:
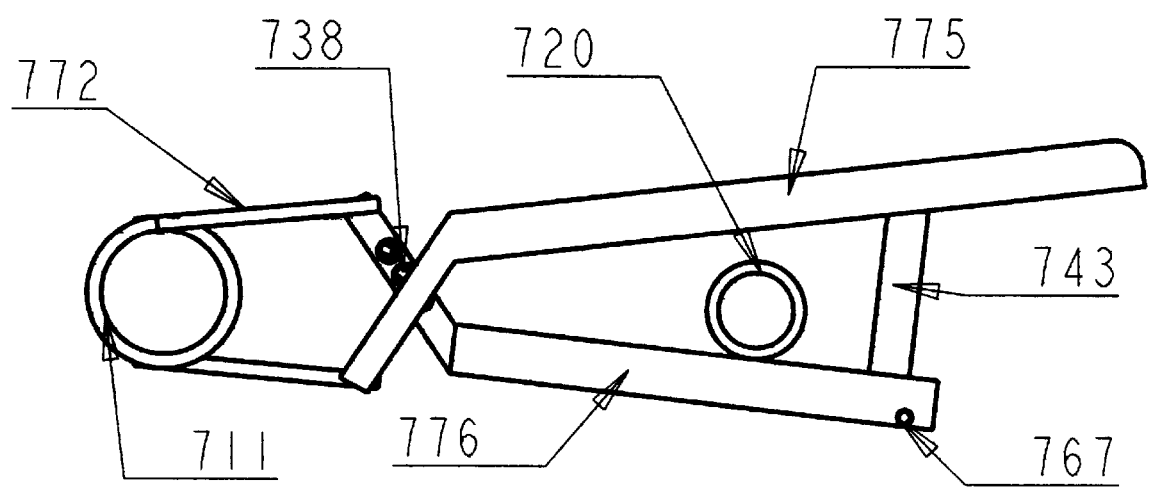
FIG. 7C is a side view of the clip of FIG. 7A with vessel guard actuated.
Figure 7:
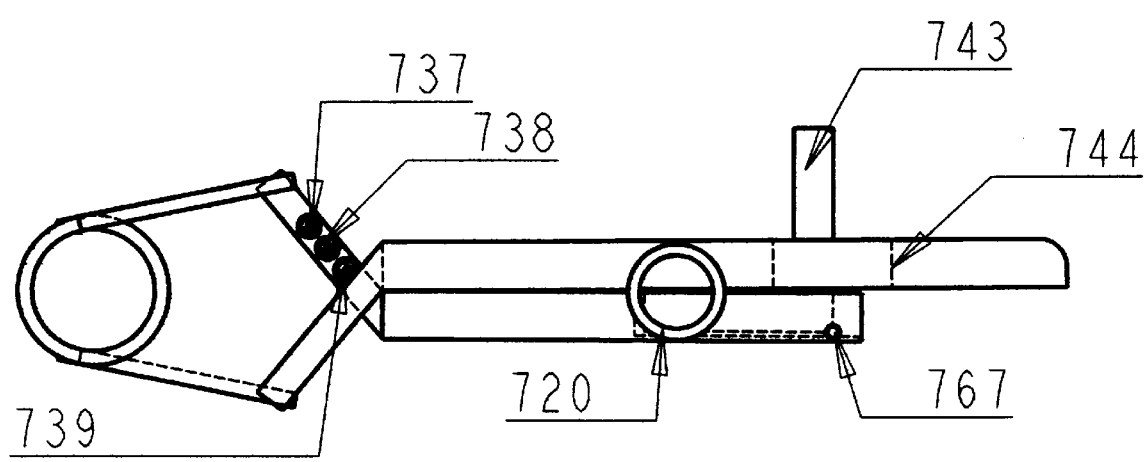
FIG. 7D is a detailed view of the clip-locking mechanism of the clip of FIG. 7A.
FIG. 7E is a detailed hidden-line side view of the clip of FIG. 7A showing the vessel-guard mechanism.

FIG. 7A illustrates the clip in its open state, ready to accept the vessel 720. FIG. 7B illustrates actuation of the vessel guard 745 by the vessel. FIG. 7C demonstrates the vessel guard 745 actuated as a fence to prevent slippage of the vessel 720 out of the clip. FIG. 7D is a cross-sectional view of the clip in an open state, gripping the vessel 720, and with the locking buttons 737, 738, 739 seen in detail. FIG. 7E shows the clip in closed state, with self-reopening prevented by the button 739.

A general concept of the invention involves employing a leakage sensing device to trigger a leakage stopping device. While a preferred embodiment accomplishes this in aneurysm surgery, other systems are possible as well. For example, a clip of the type illustrated in FIG. 1D may be used once again for aneurysm surgery with the condition that the resilient element 146 has sufficient strength that it will not automatically give way even if hemorrhage occurs. For example, the leaf spring 146 may be able to withstand a force equal to the closing force of the main spring. However, the leaf spring 146 is sufficiently ferromagnetic that an external electromagnet of sufficient power can trigger the leaf spring to pull away from the clip so that the jaws close. In this arrangement, the electromagnet is actuated by a visual detection mechanism for bleeding. The operating microscope which is used during aneurysm surgery will detect sudden significant hemorrhage by a stereotypical flash of red which consumes the entire view. An optical analyzer which measures the extent of "red" in the microscope's field can then respond to such hemorrhage by automatically activating a solenoid which in turn actuates the clip.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus for modulating flow in biological conduits, said apparatus comprising:
    a valve having an open state and a closed state, said valve configured for application to a biological conduit;
    valve control means for maintaining said valve in an open state after said valve is applied to the biological conduit;
    said valve control means automatically actuating a change of state of said valve from said open state to said closed state in response to a leakage condition in said biological conduit;
    said valve control means being simultaneously selectively manually and remotely operable to actuate a change of state of said valve from said open state to said closed state;
    said valve control means maintaining said valve in a closed state after a change of state of said valve from an open state to a closed state has occurred, and until said valve is manually or remotely operated to actuate a change of state of said valve from said closed state to said open state wherein said valve comprises a surgical clip comprising opposing upper and lower jaws for receiving the biological conduit there between, and a first resilient member connecting said upper and lower jaws, said upper and lower jaws being resiliently biased towards one another by said first resilient member.

2. The apparatus for modulating flow in biological conduits of claim 1, said valve control means further comprising:
    a plurality of protrusions interposed between the jaws of said surgical clip, and a second resilient member engaging one of said protrusions and biasing the jaws away from one another, said second resilient member having a spring constant sufficient to hold said jaws in said open state when said clip is applied to the biological conduit having therein a normal fluid pressure for said biological conduit, and said spring constant being insufficient to hold the jaws in said open state when a significantly lower-than-normal fluid pressure is experienced within said biological conduit.

3. The apparatus for modulating flow in biological conduits of claim 1, said second resilient member further comprising a leaf spring mounted within one of the jaws.

4. The apparatus for modulating flow in biological conduits of claim 3, said protrusions being mounted on biological conduit guide member pivotally mounted to a free end of one of the jaws.

5. The apparatus for modulating flow in biological conduits of claim 4, said protrusions having a first face generally perpendicular to said biological conduit guide member, and a second face arranged at an angle to said biological conduit guide member, said resilient member engaging said second face when said clip is placed on a biological conduit such that said clip is more readily changed from an open state to a closed state than it is from a closed state to an open state.

6. The apparatus for modulating flow in biological conduits of claim 2, further comprising:
    a vessel stop extending upward from said lower jaw for preventing rearward travel of said biological conduit within an opening between the jaws when said clip is applied to said biological conduit; and
    an orifice in said upper jaw for receiving said vessel stop when said clip achieves said closed state.

7. The apparatus for modulating flow in biological conduits of claim 2, further comprising:
    a vessel stop extending upward from said lower jaw for preventing forward travel of said biological conduit within an opening between the jaws when said clip is applied to said biological conduit; and
    an orifice in said upper jaw for receiving said vessel stop when said clip achieves said closed state.

8. The apparatus for modulating flow in biological conduits of claim 1, said surgical clip further comprising a first arm connecting said first resilient member to one of the jaws, and a second arm connecting said first resilient member to another of the jaws, said second arm crossing over said first arm, and said valve control means further comprising:
    a plurality of protrusions interposed between said first arm and said second arm, and a plurality of second resilient members upwardly biasing said protrusions to prevent relative movement of said first and second arms, said second resilient members having a spring constant sufficient to hold said first and second arms and the jaws in said open state when said clip is applied to a biological conduit having therein a normal fluid pressure for said biological conduit, and said spring constant being insufficient to prevent relative movement of said first and second arms and to hold the jaws in said open state when a significantly lower-than-normal fluid pressure is experienced within said biological conduit.

9. The apparatus for modulating flow in biological conduits of claim 8, said resilient member further comprising a leaf spring mounted within said first arm and biasing said protrusions into a path of travel of said second arm with respect to said first arm.

10. The apparatus for modulating flow in biological conduits of claim 9, said protrusions having a first inclined face and a second inclined face, said second inclined face having a steeper incline than said first inclined face, said second arm engaging one of said first faces when said clip is placed on the biological conduit such that said clip is more readily changed from an open state to a closed state than it is from a closed state to an open state.

11. The apparatus for modulating flow in biological conduits of claim 1, said surgical clip further comprising:
    a first arm connecting a first free end of said first resilient member to one of the jaws;
    a second resilient member extending from a second free end of said first resilient member;
    a second arm connecting said second resilient member to the other of the jaws, said second arm crossing over said first arm;
    said valve control means further comprising:
        a plurality of protrusions interposed between said first arm and said second arm, and a plurality of third resilient members upwardly biasing said protrusions to prevent relative movement of said first and second arms, said third resilient members having a spring constant sufficient to hold said first and second arms and the jaws in said open state when said clip is applied to the biological conduit having therein a normal fluid pressure for said biological conduit, and said spring constant being insufficient to prevent relative movement of said first and second arms and to hold the jaws in said open state when a significantly lower-than-normal fluid pressure is experienced within said biological conduit.

12. The apparatus for modulating flow in biological conduits of claim 1, said second resilient member further comprising a helical spring affixed to said first resilient member, said helical spring biasing the jaw attached to said first arm toward the opposite jaw.

13. The apparatus for modulating flow in biological conduits of claim 12, said helical spring further comprising a forward extension for engagement with a clip applier for depressing said first arm and widening an opening between said jaws for application of said clip to a biological conduit, said helical spring biasing said first arm back to its original position after said clip is applied to a biological conduit and said clip applier is removed to narrow a forward extent of said opening between said jaws.

14. The apparatus for modulating flow in biological conduits of claim 1, said surgical clip further comprising a first arm connecting said first resilient member to one of the jaws, and a second arm connecting said first resilient member to another of the jaws, said second arm crossing over said first arm, and said valve control means further comprising:
   a second resilient member attached to said first arm, said second resilient member having a plurality of protrusions thereon;
   a protrusion engaging member attached to a said second arm, said protrusion engaging member comprising an elongate hook lying adjacent to said second resilient member and engaging said protrusions on said second resilient member, said second resilient member being biased against said protrusion engaging member to prevent relative movement of said first and second arms, said second resilient member having a spring constant sufficient to hold said first and second arms and the jaws in said open state when said clip is applied to the biological conduit having therein a normal fluid pressure for said biological conduit, and said spring constant being insufficient to prevent relative movement of said first and second arms and to hold the jaws in said open state when a significantly lower-than-normal fluid pressure is experienced within said biological conduit.

15. The apparatus for modulating flow in biological conduits of claim 14, said second resilient member further comprising a leaf spring extending downward from said first extension of said first resilient member.

16. The apparatus for modulating flow in biological conduits of claim 16, said protrusions having a first face generally perpendicular to said leaf spring, and a second face arranged at an angle to said leaf spring, said protrusions engaging member engaging said second face when said clip is place on the biological conduit such that said clip is more readily changed from an open state to a closed state than it is from a closed state to an open state.

17. The apparatus for modulating flow in biological conduits of claim 14, said surgical clip further comprising:
   a third resilient member disposed between said first resilient member and said second arm, said third resilient member comprising a helical spring affixed to said first resilient member, said helical spring biasing the jaw attached to said second arm toward the opposite jaw.

18. The apparatus for modulating flow in biological conduits of claim 17, said helical spring further comprising a forward extension for engagement with a clip applier for depressing said second arm and widening an opening between the jaws for application of said clip to the biological conduit, said helical spring biasing said second arm back to its original position after said clip is applied to the biological conduit and said clip applier is removed to narrow a forward extent of said opening between the jaws.

19. The apparatus for modulating flow in biological conduits of claim 1, further comprising a second resilient member biasing said upper and lower jaws away from one another, said second resilient member having a spring constant sufficient to hold the jaws in said open state when said clip is applied to the biological conduit having therein a normal fluid pressure for said biological conduit, and said spring constant being insufficient to hold the jaws in said open state when a significantly lower-than-normal fluid pressure is experienced within said biological conduit.

20. The apparatus for modulating flow in biological conduits of claim 19, wherein said second resilient member is more ferromagnetic than the remainder of said clip.

21. The apparatus for modulating flow in biological conduits of claim 20, further comprising means for generating a magnetic field in exclusively electromagnetic communication with said second resilient member, said magnetic field being of sufficient strength to cause said second resilient member to effect transition of said clip to a closed state.

22. The apparatus for modulating flow in biological conduits of claim 21, wherein said means for generating a magnetic field further comprises an electrical switch for selectively activating and deactivating said magnetic field.

23. The apparatus for modulating flow in biological conduits of claim 22, wherein said switch is manually operable.

24. The apparatus for modulating flow in biological conduits of claim 22, wherein said switch mechanism further comprises sensing means for automatically operating said switch in response to a leakage condition in said biological conduit.

25. The apparatus for modulating flow in biological conduits of claim 24, said sensing means further comprising a visual monitoring device, said visual monitoring device detecting a sudden increase in the quantity of the color red in the operative field and activating said switch when said sudden increase in the quantity of the color red is detected.

26. An apparatus for modulating flow in biological conduits, said apparatus comprising:
   a valve having an open state and a closed state, said valve configured for application to biological conduit;
   valve control means for maintaining said valve in an open state after said valve is applied to the biological conduit;
   said valve control means automatically actuating a change of state of said valve from said open state to said closed state in response to a leakage condition in said biological conduit;
   said valve control means maintaining said valve in a closed state after a change of state of said valve from an open state to a closed state has occurred, and until said valve is manually or remotely operated to actuate a change of state of said valve from said closed state to said open state wherein said valve comprises a surgical clip comprising opposing upper and lower jaws for receiving the biological conduit there between, and a first resilient member connecting said upper and lower jaws, said upper and lower jaws being resiliently biased towards one another by said first resilient member.

27. The apparatus for modulating flow in biological conduits of claim 26, said surgical clip further comprising a first arm connecting said first resilient member to one of the jaws, and a second arm connecting said first resilient member to another of the jaws, said second arm crossing over said first arm, said second arm further comprising a downwardly directed lip, and said valve control means further comprising:

a plurality of protrusions interposed between said first arm and said second arm, said plurality of protrusions engaging said downwardly directed lip on said second arm, and said first resilient member biasing said lip against said protrusions, said first resilient member having a torsional spring constant sufficient to hold said first and second arms and the jaws in said open state when said clip is applied to the biological conduit, and said spring constant being insufficient to prevent relative movement of said first and second arms and to hold the jaws in said open state when a significantly lower-than-normal fluid pressure is experienced within said biological conduit.

28. The apparatus for modulating flow in biological conduits of claim 27, said protrusions having a first face generally parallel to said lip, and a second face arranged at an angle to said lip, said lip engaging said protrusions when said clip is placed on the biological conduit such that said clip is more readily changed from an open state to a closed state than it is from a closed state to an open state.

29. The apparatus for modulating flow in biological conduits of claim 26, said surgical clip further comprising a first arm connecting said first resilient member to one of the jaws, and a second arm connecting said first resilient member to another of the jaws, said second arm crossing over said first arm, and said valve control means further comprising:

a plurality of protrusions interposed between said first arm and said second arm, and a plurality of second resilient members upwardly biasing said protrusions to prevent relative movement of said first and second arms, said second resilient members having a spring constant sufficient to hold said first and second arms and the jaws in said open state when said clip is applied to the biological conduit having therein a normal fluid pressure for said biological conduit, and said spring constant being insufficient to prevent relative movement of said first and second arms and to hold the jaws in said open state when a significantly lower-than-normal fluid pressure is experienced within said biological conduit.

30. The apparatus for modulating flow in biological conduits of claim 29, said resilient member further comprising a coil spring mounted within said first arm and biasing said protrusion into a path of travel of said second arm with respect to said first arm.

31. The apparatus for modulating flow in biological conduits of claim 30, said protrusions having a first inclined face and a second inclined face, said second inclined face having a steeper incline than said first inclined face, said second arm engaging one of said first faces when said clip is placed on the biological conduit such that said clip is more readily changed from an open state to a closed state than it is from a closed state to an open state.

32. The apparatus for modulating flow in biological conduits of claim 26, said surgical clip further comprising a first arm connecting said first resilient member to one of the jaws, and a second arm connecting said first resilient member to another of the jaws, said second arm crossing over said first arm, said first resilient member having a spring constant sufficient to hold said first and second arms and the jaws in said open state when said clip is applied to the biological conduit having therein a normal fluid pressure for said biological conduit, and said spring constant being insufficient to prevent relative movement of said first and second arms and to hold the jaws in said open state when a significantly lower-than-normal fluid pressure is experienced within said biological conduit, and said valve control means further comprising:

a plurality of protrusions interposed between said first arm and said second arm, and a plurality of second resilient members upwardly biasing said protrusions to prevent relative movement of said first and second arms after said clip has achieved said closed state until said clip is manually or remotely actuated to return to an open state.

33. The apparatus for modulating flow in biological conduits of claim 32, said second resilient member further comprising a coil spring mounted within said first arm and biasing said protrusion into a path of travel of said second arm with respect to said first arm.

34. The apparatus for modulating flow in biological conduits of claim 33, said protrusions having a first inclined face and a second inclined face, said second inclined face having a steeper incline than said first inclined face, said second arm engaging one of said first faces when said clip is placed on the biological conduit such that said clip is more readily changed from an open state to a closed state than it is from a closed state to an open state.

35. The apparatus for modulating flow in biological conduits of claim 27, said surgical clip further comprising a biological conduit guide member pivotally mounted to a freed end of one of the jaws.

36. The apparatus for modulating flow in biological conduits of claim 35, said biological conduit guide member further comprising a generally L-shaped bracket pivotable from a first position wherein a rightmost portion of the bracket is parallel to said one of the jaws and a leftmost portion of the bracket is perpendicular to said one of the jaws, to a second position wherein said rightmost portion of the bracket is perpendicular to said one of the jaws and said leftmost portion of the bracket is parallel to said one of the jaws to prevent forward travel of said biological conduit out of the grasp of said clip.

37. A method for modulating flow in biological conduits comprising the steps of:

applying to a biological conduit a pinch valve having a ferromagnetic valve control means whereby said biological conduit is positioned and held between opposing jaws of said pinch valve while said pinch valve is maintained in an open position;

generating a magnetic field outside of a patient's body of sufficient magnitude so as to be in electromagnetic communication with said ferromagnetic valve control means; and allowing said magnetic field to operate said valve control means to change said pinch valve from an open state to a closed state to close said biological conduit wherein said valve comprises a surgical clip comprising opposing upper and lower jaws for receiving the biological conduit there between, and a first resilient member connecting said upper and lower jaws, said upper and lower jaws being resiliently biased towards one another by said first resilient member.

38. The method for modulating flow in biological conduits of claim 35, further comprising the steps of:

terminating said magnetic field after said pinch valve has achieved a closed state to allow said biological conduit to be inspected and repaired;

generating a second magnetic field outside of a patient's body of sufficient magnitude so as to be in electromagnetic communication with said ferromagnetic valve control means; and allowing said second magnetic field to operate said valve control means to change said pinch valve from a closed state to an open state to reopen said biological conduit.

* * * * *